(12) United States Patent  (10) Patent No.: US 7,914,989 B2
Bortolin et al.  (45) Date of Patent: Mar. 29, 2011

(54) CAPTURE MOIETIES FOR NUCLEIC ACIDS AND USES THEREOF

(75) Inventors: Susan Bortolin, Oakville (CA); Roman L. Zastawny, Etobicoke (CA)

(73) Assignee: Luminex Molecular Diagnostics, Inc., Toronto (CA)

( * ) Notice: Subject to any disclaimer, the term of this patent is extended or adjusted under 35 U.S.C. 154(b) by 924 days.

(21) Appl. No.: 11/807,328

(22) Filed: May 25, 2007

(65) Prior Publication Data

US 2008/0051568 A1  Feb. 28, 2008

Related U.S. Application Data

(63) Continuation of application No. 10/297,539, filed as application No. PCT/CA01/00820 on Jun. 6, 2001, now Pat. No. 7,230,092.

(60) Provisional application No. 60/209,595, filed on Jun. 6, 2000.

(51) Int. Cl.
 C12Q 1/68 (2006.01)
 C12P 19/34 (2006.01)
 C07H 21/02 (2006.01)
 C07H 21/04 (2006.01)
 C07H 21/00 (2006.01)

(52) U.S. Cl. ......... 435/6; 435/91.1; 536/23.1; 536/24.3; 536/24.33; 536/25.3

(58) Field of Classification Search ............ 435/6, 91.1, 435/183; 436/94, 501; 536/23.1, 24.3, 24.33, 536/25.3
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 5,374,524 A | 12/1994 | Miller |
| 5,604,097 A | 2/1997 | Brenner et al. |
| 5,635,400 A | 6/1997 | Brenner et al. |
| 5,654,413 A | 8/1997 | Brenner et al. |
| 5,770,365 A | 6/1998 | Lane et al. |
| 5,866,336 A | 2/1999 | Nazarenko et al. |
| 5,925,517 A | 7/1999 | Tyagi et al. |
| 6,025,133 A | 2/2000 | Stull et al. |
| 6,063,571 A | 5/2000 | Uhlmann et al. |
| 6,063,604 A | 5/2000 | Wick et al. |
| 6,138,077 A | 10/2000 | Brenner et al. |
| 6,150,516 A | 11/2000 | Brenner et al. |

(Continued)

FOREIGN PATENT DOCUMENTS

WO  WO-9802449  1/1998

OTHER PUBLICATIONS

Bell et al. (1981) Proc. Nat. Acad. Sci. USA 78: p. 5759-5763.

(Continued)

*Primary Examiner* — Frank W Lu
(74) *Attorney, Agent, or Firm* — Goodwin Procter LLP

(57) ABSTRACT

A unimolecular probe for hybridization to a molecule comprising a target nucleic acid sequence, the probe includes: a first nucleic acid sequence complementary to the target sequence (target-binding sequence); and a second nucleic acid sequence complementary to a portion of the first nucleic acid sequence and capable of hybridization therewith to form a first intramolecular duplex. In use, the target and target-bind sequence hybridize to form a duplex. A probe can be used to detect a molecule containing the target sequence, act as a primer for synthesis or amplification, etc.

27 Claims, 12 Drawing Sheets

U.S. PATENT DOCUMENTS

| | | | |
|---|---|---|---|
| 6,172,214 | B1 | 1/2001 | Brenner et al. |
| 6,200,753 | B1 | 3/2001 | Nathan et al. |
| 6,232,462 | B1 | 5/2001 | Collins et al. |
| 6,235,475 | B1 | 5/2001 | Brenner et al. |
| 6,235,480 | B1 | 5/2001 | Shultz et al. |
| 6,288,220 | B1 | 9/2001 | Kambara et al. |
| 6,307,041 | B1 | 10/2001 | Ruffner et al. |
| 6,500,622 | B2 | 12/2002 | Bruchez, Jr. et al. |
| 7,230,092 | B2 | 6/2007 | Bortolin et al. |

OTHER PUBLICATIONS

Bonnet et al.(1999) Proc. Natl. Acad. Sci. USA 96:6171-6176.
Cantor and Schimmel; Biophysical Chemistry; Part III, p. 1183 (1980).
Doktycz et al. (1993) Biopolymers 33: p. 1765.
Figures 1 and 2 from US Patent No. 6,500,622 B2 with the examiner's handwritings.
International Search Report (EPO as ISA), published in connection with PCT/CA 01/00820 on Dec. 13, 2001.
Khrapko et al. (1991) J. DNA Sequencing Mapping 1: p. 375-388.
Maniatis et al.; Molecular Cloning: A Laboratory Manual, Cold Spring Harbor Laboratory (1989).
Mir and Southern (1999) Nature Biotech; 17: p. 788-792.
Lane et al. (1997) Nucleic Acids Res. 25(3): 611-617.
Newton et al.; PCR, 2.sup.nd Ed., Springer-Verlag (New York: 1997), p. 24.
Saiki (1985) Science 230: p. 1350-1355.

Match
 4a
 4b
 4c
 3a
 3b
 3c
 3d
 3e
 3f
 2a
 2b
 2c
 2d

CAPTURE MOIETIES FOR NUCLEIC ACIDS AND USES THEREOF

CROSS-REFERENCE TO RELATED APPLICATIONS

This application is a continuation of U.S. patent application Ser. No. 10/297,539 filed Dec. 6, 2002 and now U.S. Pat. No. 7,230,092, which is a national stage application of PCT/CA01/00820, filed Jun. 6, 2001, which claims the benefit of and priority under 35 U.S.C. §119(e) to U.S. provisional patent application Ser. No. 60/209,595, filed Jun. 6, 2000. The entire disclosure of U.S. patent application Ser. No. 10/297,539 is incorporated by reference herein.

FIELD OF THE INVENTION

The present invention is in the field of molecules, such as probes, that hybridize to other molecules containing target nucleic acid sequences. A probe can be used to determine the presence or absence of a particular target sequence in a sample, as a primer for synthesis or amplification of a nucleic acid molecule containing the target, etc. A probe can be used to distinguish closely related targets that may be present in a sample.

BACKGROUND OF THE INVENTION

Methods of detecting sequences of nucleic acids are of wide applicability in research and medical fields. Nucleic acid analysis has been applied in areas such as detection of single nucleotide polymorphisms (SNP's), infectious disease screening, diagnosis and prognosis of genetic disease and assessment of treatment. The ability to identify nucleic acid sequences at the single base level for an increasing number of positions within a particular genome is required.

The demand for nucleic acid-based technologies with diagnostic and microarray capabilities is on the rise. This can be partly attributed to the Human Genome Project, which has been instrumental in prompting further investigation into such areas as the genetic basis of disease, genetic predisposition to disease and pharmacogenomics. There is a need for easy-to-use, low-cost, clinically relevant tests that are highly sensitive and specific.

Hybridization, the intermolecular association of nucleic acid molecules through hydrogen bonding of nucleic acid bases between molecules underlies many of the most promising analytical techniques. The overall success of any hybridization-based assay relies on a number of factors. In an ideal system, the hybridization is very sensitive, i.e., hybridization between a capture moiety and its target occurs readily. The hybridization should also be very specific, i.e., hybridization between the capture moiety and molecules which are not a target can be largely avoided.

Molecular biological techniques have been developed which employ enzyme-mediated target amplification strategies to increase the copy number of a specific analyte. This generally increases the ease with which the amplified analyte can be detected or otherwise manipulated. Examples of such techniques include the polymerase chain reaction (PCR), ligase chain reaction (LCR), transcription-mediated amplification (TMA), strand-displacement amplification (SDA) and nucleic-acid sequence-based amplification (NASBA). However, all of these technologies are based on linear probe sequences, and have their limitations particularly with respect to issues relating to specificity. This is because incorrect hybridization can lead to amplification of an undesired analyte.

Attempts have been made, with varying degrees of success, to increase the sensitivity and specificity of nucleic acid hybridization processes. For example, Lane et al. have suggested a nucleic acid capture moiety that includes a hairpin duplex adjacent to a single stranded region complementary to a target sequence. Further, the inclusion of an element capable of stabilizing the intermolecular duplex, once formed was suggested (NAR 1997; 25: 611-16, U.S. Pat. No. 5,770,365). Other approaches include nucleotide analogues that enhance thermal stability differences with the idea of improving the discrimination of single nucleotide polymorphisms. Adjusting buffer components, temperature, electrical potential etc. have also been used to enhance mismatch discrimination.

Current technologies which control for specificity of hybridization rely mainly on modification of environmental conditions such as temperature, salt concentration, addition of DNA-specific condensing (TMAC) or denaturing agents (formamide). These technologies, while adequately controlling individual nucleic acid tests, lack the ability to control complex mixtures of DNA tests to the same level of accuracy. For instance, temperature for hybridization needs to be controlled closely, preferably to better than +/−1° C. However, differences in base composition of probe moieties continue to make it difficult to obtain optimum conditions for the use of many probes in a single mixture. To reduce $T_m$ differences associated with nucleotide compositions of probe moieties, chaotropic agents have been used. Quaternary or tertiary amine salts such as tetramethylammoniumchloride (TMAC) have been used with some success.

Duplex denaturing reagents, such as formamide, can increase the specificity of target binding to its cognate probe capture moiety. In this approach, a duplex denaturant is used to destabilize duplex formation, particularly duplexes resulting from hybridization of mismatched nucleic acid sequences.

Also attempted, has been the design of sequences which minimally cross-hybridize with each other. Such families of sequences can be used as 'zipcodes', 'barcodes' or 'tags' that are associated with the target and subsequently hybridized to the anti-tag (tag complement) found on the microarray, bead, etc. Families of nucleic acid tags wherein each member of the tag family varies from every other member of the family by a particular minimum number of bases (comparing tags in end-to-end alignment) have been described. See, for example, U.S. Pat. No. 5,604,097, Brenner, U.S. Pat. No. 5,635,400, Brenner, U.S. Pat. No. 5,654,413, Brenner, U.S. Pat. No. 6,138,077, Brenner; U.S. Pat. No. 6,150,516, Brenner et al.; U.S. Pat. No. 6,172,214, Brenner; and U.S. Pat. No. 6,235,475, Brenner et al.

Another probe, called a molecular beacon, is a single stranded stem and loop structure with a fluorophore attached to one end and a quencher attached to the other (Tyagi et al. U.S. Pat. No. 5,925,517). The principle for target detection is based on the hybridization of the target sequence to the single stranded loop forcing the stem to unwind resulting in fluoresence. Optimal position of the mismatch within the loop region has been studied (Bonnet et al. Proc. Natl. Acad. Sci. USA. 1999. 96:6171-6176).

Especially valuable to modern genomics technologies, such as biochips or DNA microarrays that process larger numbers would be probes that permit many (100's to 100,000's) of tests to be run in parallel. Also valuable would be probes that reliably discriminate between sequences that differ from each other by only one nucleotide, such as SNPs.

SUMMARY OF THE INVENTION

A unimolecular probe for hybridization to a molecule comprising a target nucleic acid sequence, the probe includes:
 (i) a first nucleic acid sequence complementary to the target sequence; and
 (ii) a second nucleic acid sequence complementary to a portion of the first nucleic acid sequence and capable of hybridization therewith to form a first intramolecular duplex under a defined set of conditions; and wherein:
 (iii) hybridization of the target and first sequences to form an intermolecular duplex occurs under said set of conditions.

A probe can be used for detecting the presence or absence in a sample of a molecule containing the target nucleic sequence. A probe can be used as a primer for synthesis, as for example in an amplification scheme, of a molecule containing the target. A specific application may be in aid of diagnosing a disease, for example, determining whether a biological sample contains a target nucleic acid sequence specific for a disease associated with the expression of one or more genes. A probe can be included in a family or repertoire of probes that are used together, for example, in simultaneous screening for several targets, or as complements of tags.

The sequence of a probe complementary to the target sequence is sometimes referred to herein as the "target-binding" site, sequence or region. One can see that because the second nucleic acid is complementary to only a portion of the target sequence, part of the target sequence of the probe does not enter into intramolecular bonding and thus act as a nucleation site for binding of the target to the probe.

In another aspect, the invention is unimolecular probe for detecting the presence or absence in a sample of a target molecule comprising a target nucleic acid, the probe comprising a molecule selected from the group consisting of: A-B-C-D-E-F-G, D-E-F-G, and E-F-G, wherein:
 (i) each of A, C, D, E and G is a nucleic sequence;
 (ii) E and G are complementary to each other and covalently linked to each other by F so as to form a first intramolecular duplex under a defined set of conditions;
 (iii) (a) for the molecule E-F-G, the entirety of sequence E and at least a portion of F together form a nucleic acid sequence substantially complementary to the target nucleic acid sequence of the target molecule, and the molecule E-F-G and the target molecule hybridize with each other such that the probe and target molecule form an intermolecular duplex under said conditions;
 (b) for each of the molecules A-B-C-D-E-F-G and D-E-F-G, (1) the entirety of sequence E and at least a portion of D, or (2) the entirety of sequence E and at least a portion of D and at least a portion of F, together form a nucleic acid sequence substantially complementary to the target nucleic acid sequence of the target molecule, and each of the molecules A-B-C-D-E-F-G and D-E-F-G, and the target molecule, hybridize with each other such that the probe and target molecule form an intermolecular duplex under said conditions; and
 (c) A and C of the molecule A-B-C-D-E-F-G are complementary to each other and covalently linked to each other by B so as to form a second intramolecular duplex under said set of conditions.

A probe of the invention may be a part of repertoire of probes, for use in large-scale screening or detection of target sequences.

The invention thus includes a repertoire of populations of oligonucleotide tags, each tag of a population comprising a probe of the invention, wherein each tag in a population contains a nucleic acid sequence substantially complementary to a target nucleic acid sequence and the target molecule for the a tag of each population is different for each population.

It will, of course, be understood that a family of probes making up a family of "tags" can also be used as family of "tag complements". It is likely the case, however, that a family of sequences of the invention in this context would be used as tag complements, rather than the tags which are normally considered that component attached directly to an element to be harvested by means of the tag-tag complement combination.

In another embodiment, the invention is a kit for determining the presence in a sample of a first molecule containing a target nucleic acid sequence. The kit includes;
 (1) a probe for determining the presence of the first molecule, the probe comprising:
  (i) a first nucleic acid sequence complementary to the target sequence; and
  (ii) a second nucleic acid sequence complementary to a portion of the first nucleic acid sequence and capable of hybridization therewith to form a first intramolecular duplex under a defined set of conditions; and wherein:
  (iii) hybridization of the target and first sequences to form an intermolecular duplex occurs under said set of conditions;
 (2) a second molecule comprising a control nucleic acid sequence, the control nucleic acid sequence being different from the target nucleic acid sequence; and
 (3) a probe for determining the presence of the second molecule, the probe comprising:
  (i) a third nucleic acid sequence complementary to the control sequence; and
  (ii) a fourth nucleic acid sequence complementary to a portion of the third nucleic acid sequence and capable of hybridization therewith to form a first intermolecular duplex under said set of conditions; and wherein:
  (iii) hybridization of the control and third sequences to form an intermolecular duplex occurs under said set of conditions.

In another aspect, the invention is a kit for sorting and identifying polynucleotides. The kit includes:
a solid phase support having one or more spatially discrete regions, each such region having a uniform population of substantially identical probes covalently attached, wherein each probe is a unimolecular moiety comprising:
 (i) a first tag sequence complementary to a target sequence of said polynucleotide to be identified; and
 (ii) a nucleic acid second sequence complementary to a portion of the first tag sequence and capable of hybridization therewith to form a first intramolecular duplex under a defined set of conditions; and wherein:
 (iii) hybridization of the target and tag sequences to form an intermolecular duplex occurs under said set of conditions.

In another embodiment, the invention is a composition comprising a mixture of a plurality of microparticles, each microparticle having a probe attached thereto for detection of a target nucleic acid sequence, each probe comprising a single molecule comprising:

(i) a first tag sequence complementary to the target sequence; and
(ii) a nucleic acid second sequence complementary to a portion of the first tag sequence and capable of hybridization therewith to form a first intramolecular duplex under a defined set of conditions; and wherein:
(iii) hybridization of the target and tag sequences to form an intermolecular duplex occurs under said set of conditions.

In another embodiment, the invention is a repertoire of oligonucleotide tag complements, each complement belonging to a population of like complements and being a unimolecular moiety comprising:
(i) a first complement sequence complementary to a target tag sequence; and
(ii) a nucleic acid second sequence complementary to a portion of the first complement sequence and capable of hybridization therewith to form a first intramolecular duplex under a defined set of conditions; and wherein:
(ii) hybridization of the complement and tag sequences to form an intermolecular duplex occurs under said set of conditions;
wherein there are at least ten said populations of tag complements, each tag of a population having a said complement sequence different from the complement sequence of the tags in every other population in the repertoire.

In yet another embodiment, the invention is a method of detecting a molecule comprising a target nucleic acid sequence. The method includes:
providing a sample that may contain the molecule;
providing a suitable probe according to the invention, having a sequence complementary to that of the template;
exposing the sample and probe to conditions suitable for the formation of an intermolecular duplex therebetween; and
detecting the absence or presence of the intermolecular duplex.

The method of detecting the intermolecular duplex is accomplished through any appropriate means, there being many available to the skilled person.

In another particular embodiment, the invention is a method for detecting a single-stranded nucleic acid target sequence. This method includes:
(a) providing a nucleic acid capture moiety comprising a unimolecular moiety comprising:
(i) a first nucleic acid sequence complementary to the target sequence; and
(ii) a second nucleic acid sequence complementary to a portion of the first nucleic acid sequence and capable of hybridization therewith to form a first intramolecular duplex under a defined set of conditions; and wherein:
(iii) hybridization of the target and first sequences to form an intermolecular duplex occurs under said set of conditions;
(b) forming a reaction mixture comprising the single-stranded target nucleic acid and nucleic acid capture moiety under conditions such that the duplex of (a)(iii) forms;
(c) detecting the presence or absence of the duplex of (b); such that the target single-stranded nucleic acid is detected.

Another embodiment of the invention is a method of synthesizing a nucleic acid molecule, the method comprising:
(a) providing a sample containing or suspected of containing the nucleic acid to be synthesized;
(b) providing a probe comprising a unimolecular capture moiety comprising:
(1) a first nucleic acid sequence complementary to a sequence of the nucleic acid molecule to be synthesized so as to act as primer for said synthesis; and
(2) a second nucleic acid sequence complementary to a portion of the first nucleic acid sequence and capable of hybridization therewith to form a first intramolecular duplex under a set of conditions suitable for said synthesis; and
(c) exposing the sample and probe to said conditions so as to synthesize the nucleic acid molecule.

Another embodiment of the invention is a method of detecting first and second target sequences comprising first and second target nucleic acid sequences, the method comprising:
(a) providing a sample that may contain the first and second sequences;
(b) providing first and second probes, wherein:
(i) the first probe comprises a unimolecular capture moiety comprising:
(1) a first nucleic acid sequence complementary to the first target sequence; and
(2) a nucleic acid sequence complementary to a portion of the first nucleic acid sequence and capable of hybridization therewith to form an intramolecular duplex therewith under a defined set of conditions;
(ii) the second probe comprises a unimolecular capture moiety comprising:
(3) a second nucleic acid sequence complementary to the second target sequence; and
(4) a nucleic acid sequence complementary to a portion of the second nucleic acid sequence and capable of hybridization therewith to form an intramolecular duplex therewith under said set of conditions; wherein:
(iii) hybridization of the first target and first nucleic acid sequences to form a first intermolecular duplex occurs under said set of conditions, and hybridization of the second target and second nucleic acid sequences to form a second intermolecular duplex occurs under said set of conditions; and
(iv) the first and second target sequences differ from each other by at least one nucleotide base; and
(c) detecting the absence or presence of each of the first and second intermolecular duplexes.

Probes of the invention include embodiments suitable for use as primers in primed synthesis reactions, such as PCR. In this context, a probe or capture moiety of the invention functions as a primer, that is, the probe hybridizes to a target sequence that is part of a sequence to be amplified and a polymerase extends the primer using the remainder of the molecule containing the target sequence as a template. In amplification reactions, it is usually the case that two primers are used.

An embodiment of the invention is thus a method of synthesizing a nucleic acid molecule, the method comprising:
(a) providing a sample containing or suspected of containing the nucleic acid to be synthesized;
(b) providing a probe comprising a unimolecular capture moiety comprising:
(1) a first nucleic acid sequence complementary to a sequence of the nucleic acid molecule to be transcribed so as to act as primer for said synthesis; and
(2) a second nucleic acid sequence complementary to a portion of the first nucleic acid sequence and capable of hybridization therewith to form a first intramolecular duplex under a set of conditions suitable for said synthesis; and (c) exposing the sample and probe to said conditions so as to synthesize the nucleic acid molecule.

Another embodiment of the invention is a process for amplifying nucleic acids comprising:

(1) providing a nucleic acid template;
(2) hybridizing at least one primer to the 3'-end of the template, wherein the primer comprises:
   (i) a nucleic acid sequence complementary to said 3'-end of the template and having a free 3'-hydroxyl;
   (ii) a nucleic acid sequence complementary to a portion of the nucleic acid sequence of (i) and capable of hybridization therewith to form a first intramolecular duplex under a set of conditions suitable for amplifying the nucleic acid molecule; and
(3) amplifying the primer-template hybrid using at least one temperature-stable polymerase enzyme to produce linear amplification products.

As mentioned above, amplification has been used to increase the sensitivity of nucleic acid assays and the polymerase chain reaction, or PCR, is commonly used (Mullis et al. U.S. Pat. Nos. 4,683,202 and 4,683,195 and Methods in Enzymology, Volume 155, 1987, pages 335-350.) The procedure uses repeated cycles of primer dependent nucleic acid synthesis occurring simultaneously using each strand of a complementary sequence as a template, thus requiring to primers. The sequence amplified is defined by the primer molecules that initiate synthesis. The primers are complementary to the 3'-end portion of a target sequence or its complement and must hybridize with those sites in order for nucleic acid synthesis to begin. After extension product synthesis, the strands are separated, generally by thermal denaturation, before the next synthesis step. In the PCR procedure, copies of both strands of a complementary sequence are synthesized.

Another embodiment of the invention is thus a method of amplifying a nucleic acid molecule, the method comprising:

(a) providing a sample suspected of containing or known to contain the nucleic acid molecule to be amplified;
(b) providing first and second probes, wherein:
   (i) the first probe comprises a unimolecular capture moiety comprising:
      (1) a forward primer; and
      (2) a nucleic acid sequence complementary to a portion of the forward primer and capable of hybridization therewith to form a first intramolecular duplex under a set of conditions suitable for amplifying the nucleic acid molecule;
   (ii) the second probe comprises a unimolecular capture moiety comprising:
      (3) a reverse primer, and
      (4) a nucleic acid sequence complementary to a portion of the reverse primer and capable of hybridization therewith to form a first intramolecular duplex under said set of conditions; wherein:
(c) exposing the sample and first and second probes to said conditions so as to amplify the nucleic acid molecule.

Embodiments of the invention include methods for diagnosing a disease along the lines described by Uhlmann et al., in U.S. Pat. No. 6,063,571, which issued May 16, 2000, except using primers of the present invention adapted to the approach.

The invention thus includes a method of diagnosing a disease comprising:

(1) obtaining a nucleic acid template from a biological sample;
(2) mixing, under a defined set of condition, at least one primer, specific for the disease associated with the expression of one or more genes, with the sample, the primer comprising:
   (i) a first nucleic acid sequence complementary to the template; and
   (ii) a second nucleic acid sequence complementary to a portion of the first nucleic acid sequence and capable of hybridization therewith to form a first intramolecular duplex under the set of conditions; and wherein:
   (iii) hybridization of the target and first sequences to form an intermolecular duplex occurs under said set of conditions; and
(3) detecting the presence or absence of the intermolecular duplex of (2)(iii) in order to determine the presence or absence of the template in the biological sample of (1).

Another embodiment of the invention is a method of diagnosing a disease that includes:

(1) obtaining a nucleic acid template from a biological sample;
(2) mixing at least one primer, specific for the disease associated with the expression of one or more genes, with the sample to form a primer-template hybrid, the primer comprising:
   (i) a nucleic acid sequence complementary to a 3'-end of the template and having a free 3'-hydroxyl;
   (ii) a nucleic acid sequence complementary to a portion of the nucleic acid sequence of (i) and capable of hybridization therewith to form an intramolecular duplex under conditions in which the primer-template hybrid forms; and
(3) amplifying the primer-template hybrid using at least one temperature-stable polymerase enzyme to produce amplification products.

In the case of a probe of the invention having two hairpins, in which the duplex of one hairpin is determined to be less stable than that of the other hairpin by means of calculation of $T_m$, the calculation can be made according to the equation: $T_m=[(\text{number of A+T})\times 2°\text{ C.}+(\text{number of G+C})\times 4°\text{ C.}]$. See C. R. Newton et al. PCR, 2.sup.nd Ed, Springer-Verlag (New York: 1997), p. 24. The duplex with the higher $T_m$ is the more stable.

DETAILED DESCRIPTION OF THE INVENTION

Figure 1A:
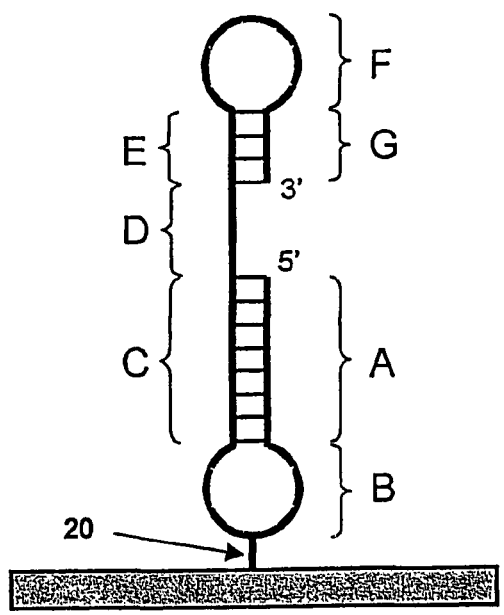
FIGS. 1A to 1D schematically illustrate four preferred embodiment capture moieties of the present invention, each anchored to a solid support. The FIG. 1A embodiment probe includes two hairpins ($HP^2$) and a target-binding, or target capture region D-E-F running in the 5'-3' direction from the anchor region. The FIG. 1B embodiment is similar to the FIG. 1A embodiment, but the target-binding region D-E-F runs in the 3'-5' direction away from the anchor region. The FIG. 1C embodiment includes only 1 hairpin and the target-binding region D-E-F runs in the 5'-3' direction away from the anchor point. The FIG. 1D embodiment also includes only 1 hairpin ("linear loop"), but the target-binding region D-E-F runs in the 3'-5' direction away from the anchor point of the probe. All probes include a region "G" complementary to region "E", which hybridize with one another to form a duplex.

The invention includes a probe and methods of using the probe.

A probe of a single type can be useful by itself in hybridizing with its target in a complex mixture. Probes of various types can be used simultaneously in hybridizing to their targets.

The target of a probe is most often a nucleic acid strand. The term "nucleic acid strand", as used herein, refers to a strand of DNA or RNA, or a chimeric DNA-RNA strand or nucleic acid-like compounds such as peptide nucleic acids. (U.S. Pat. No. 6,063,604 of Wick et al.) A nucleic acid strand can also include modified DNA or RNA bases, of which many are known in the art. It is important that such a base is capable of hybridization to its complement by hydrogen-bonding (e.g. Watson-Crick base-pairing) such that it is possible to form an intermolecular duplex between nucleic acid strands of a perfectly-matched target and target-binding site of a probe of the invention.

The term "target nucleic acid sequence" or simply "target" refers to the nucleic acid sequence which is to be detected. The target nucleic acid sequence may be any nucleic acid strand and, in general, will be single-stranded or will be made single-stranded by methods known in the art. The target nucleic acid sequence may be obtained from various sources including plasmids, viruses, bacteria, fungi, yeast, plants, and animals, including humans; or the target nucleic acid sequence can be obtained from non-natural sources. The target nucleic acid sequence can be obtained from various organisms or tissues, including fluids such as blood, semen, urine and the like. The target nucleic acid sequence is preferably extracted or purified to remove or reduce contaminating or interfering materials such as proteins or cellular debris. Procedures for such purification or extraction are known in the art, including, for example, those described in Maniatis et al., "Molecular Cloning: A Laboratory Manual", Cold Spring Harbor Laboratory (1989), or in Bell et al., *Proc. Nat. Acad. Sci. USA* (1981), 78: 5759-5763. The methods and compositions of the present invention are particularly useful in assay formats where the specific detection of multiple nucleic acid sequences is desired such as with microarrays or in the detection of genetic disorders or cellular conditions such as cancer which are characterized by single nucleotide polymorphisms. The target of a probe of the invention may be one of a family of nucleic acid molecules that have been designed to work together, and which have been selected as a group for their minimally cross-hybridizing characteristics.

As described elsewhere in detail, a probe of the invention includes internal nucleic acid sequences such that the probe forms at least one "hairpin" structure. A "hairpin", as used herein, refers to a unimolecular nucleic acid-containing structure which comprises at least two mutually complementary nucleic acid regions such that at least one intramolecular duplex can form. Hairpins are described in, for example, Cantor and Schimmel, "Biophysical Chemistry", Part III p. 1183 (1980). In certain embodiments, the mutually complementary nucleic acid regions are connected through a nucleic acid strand, in these embodiments, the hairpin comprises a single strand of nucleic acid. See, for example, region F of the probe shown in FIG. 1C. A region of the capture moiety which connects regions of mutual complementarity is referred to herein as a "loop" or "linker". In preferred embodiments, a loop is a strand of nucleic acid or modified nucleic acid. In preferred embodiments, the linker is not a hydrogen bond. In other embodiments, the loop includes a linker region which is not nucleic-acid-based; however, capture moieties in which the loop region is not a nucleic acid sequence are referred to herein as hairpins. Examples of non-nucleic-acid linkers suitable for use in the loop region are known in the art and include, for example, alkyl chains (see, e.g., Doktycz et al. (1993) Biopolymers 33:1765).

A particular preferred embodiment of the invention is a probe capable of forming two hairpins, HP$^2$. In such embodiments, a first of the hairpins includes at least a portion of the target-binding site of the probe. The first hairpin is less stable than the second hairpin. The term "less stable duplex" means that the duplex region of the first hairpin has a melting temperature ($T_m$) that is lower than that of the more stable duplex. Preferably, the $T_m$ of the less stable duplex is also lower than that of the intermolecular duplex formed between the capture moiety and the target nucleic acid. Melting temperature refers to the temperature at which 50% of the hybridized duplex is dissociated and is dependent on such parameters as nucleic acid length, composition, and sequence as well as the salt conditions under which the hybridization reaction is taking place. For comparative purposes between duplexes, hybridization conditions used would be the same.

The invention features a nucleic acid capture moiety, which has at least one nucleic acid region substantially complementary to a target nucleic acid. Two nucleic acid regions within this target binding are capable of forming an intramolecular duplex. The term "nucleic acid capture moiety" or simply "capture moiety", as used herein, refers to a moiety which binds selectively to a target nucleic acid sequence. Optionally, the moiety can be immobilized on an insoluble support, as in a microarray or to microparticles, such as beads. When used as a primer, a probe of the invention would likely not be anchored to a solid support. A capture moiety can "capture" a target nucleic acid by hybridizing to the target. In cases wherein the moiety itself is immobilized, the target too becomes immobilized. Such binding to a solid support may be through a liking moiety which is bound to either the capture moiety or to the solid support.

In preferred embodiments, the nucleic acid capture moiety is derivatized to allow binding to a solid support. Many methods of derivatizing a nucleic acid for binding to a solid support are known in the art. The capture moiety may be bound to a solid support through covalent or non-covalent bonds. In a preferred embodiment, the nucleic acid capture moiety is covalently bound to biotin to form a biotinylated conjugate. The biotinylated conjugate is then bound to a solid surface, for example, by binding to a solid, insoluble support derivatized with avidin or streptavidin. The capture moiety can be conveniently derivatized for binding to a solid support by incorporating modified nucleic acids in the loop region or in the terminal base positions of the capture moiety. When the capture moiety comprises two loops the preferred point of attachment is through the loop of the more stable hairpin.

Thus, in a preferred embodiment, the capture moiety is derivative in the loop region to permit binding to a solid support. When the loop region is complementary to the target the preferred location within the loop for derivatizing and subsequent binding to a solid support is at the end of the loop distal to the target binding region E as indicated by M in FIG. 11. In other preferred embodiments, the capture moiety is derivatized in a region other than the loop or linker region. For example, biotin-modified nucleic acids can be incorporating into the loop region to permit binding to a streptavidin-coated solid support. As noted above, a variety of moieties useful for binding to a solid support (e.g., biotin, antibodies, and the like), and methods for attaching them to nucleic acids, are known in the art. For example, an amine-modified nucleic acid base (available from, e.g., Glen Research) can be attached to a solid support (for example, Covalink-NH, a polystyrene surface grafted with secondary amino groups, available from Nunc) through a bifunctional crosslinker (e.g., bis(sulfosuccinimidyl suberate), available from Pierce). In another example, a sulfhydryl-functionalized hairpin (obtained by treating an amine-functionalized hairpin as described above with Traut's reagent (2-iminothiolane.HCl)) can be attached to a maleimide-coated polystyrene plate, available from, e.g., Corning-Costar. Additional spacing moieties can be added to reduce steric hindrance between the capture moiety and the surface of the solid support.

In certain embodiments, the capture moiety may be labelled, as with, e.g., a fluorescent moiety, a radioisotope (e.g., $^{32}$P), an antibody, an antigen, a lectin, an enzyme (e.g., alkaline phosphatase or horseradish peroxidase, which can be used in calorimetric methods), chemiluminescence, bioluminescence or other labels well known in the art. In certain embodiments, binding of a target strand to a capture moiety can be detected by chromatographic or electrophoretic methods, although this is not preferred. In embodiments in which the capture moiety does not contain a detectable label, the target nucleic acid sequence may be so labelled, or, alternatively, labelled secondary probes may be employed. A "secondary probe" includes a nucleic acid sequence which is complementary to either a region of the target nucleic acid sequence or to a region of the capture moiety. Region G of a probe (which will most often not be complementary to the target, might be useful in capturing a secondary labelled nucleic acid probe.

In preferred embodiments, the nucleic acid capture moiety whose target binding region is able to form an intramolecular duplex incorporates an additional "hairpin" stem. In other words, the method of the invention uses a "double hairpin" composed of a highly stable intramolecular duplex (ie. the stem) at one end, connected to a less stable intramolecular duplex at the opposite end through a single-stranded nucleic acid region. Alternatively the method uses a "linear loop" composed of a single intramolecular duplex containing at least a portion of the target-binding region and a single stranded region. A probe of the invention includes a nucleic acid sequence of the target-binding site that does not undergo intramolecular hybridization with another portion of the probe. This region is referred to as a "nucleation" region. This portion of the probe can be immediately adjacent to (i.e., contiguous with) either end of the portion of the target-binding site that undergoes duplex formation with another part of the probe. In other words, there can be nucleation region within region F (see any of FIGS. 1A to 1D), there can be a nucleation site within region D, or there can be a nucleation site in both of regions D and F. In this third arrangement, region D-E-F include contiguous portions which together make up the target-binding site of the probe. Duplex formation between the target and probe thus propagates outward from a nucleation site (ie. zippering) (Mir and Southern 1999. Nature Biotech. 17:788-792).

The size or configuration of a loop or linker is thus selected to allow the adjacent regions of mutual complementarity to form an intramolecular duplex of the hairpin. In embodiments in which the loop is a nucleic acid strand, the loop comprises at least 2 nucleotides, preferably 2 to 20 nucleotides and more preferably 3 to 8 nucleotides.

"Substantially complementary" means capable of forming a hybrid stable enough to allow for propagation of duplex formation between target and probe under the conditions employed. The nucleation site of a probe of the invention should be long enough to allow a matching target to bind. The nucleation site should be at least 3 bases, more preferably 5 bases, but fewer than 8 bases in length. The orientation of the nucleic acid capture moiety and hence the target binding region can be in either the 5'-3' or 3'-5' direction.

The number of base pairs in the more stable duplex region of an $HP^2$ probe is be chosen to assure the desired relative stability of duplex stem formation. To prevent hybridization of non-target nucleic acids with the intramolecular duplex-forming region of the more stable hairpin stem, the duplex forming region includes, preferably, at least a 12 base pair duplex region and has at least 50 percent G:C content, thereby conferring exceptional stability on the intramolecular duplex relative to the less stable hairpin of an $HP^2$ embodiment probe. In preferred embodiments, the highly stable intramolecular duplex stem is less than 30 base pairs, more preferably less than 20 base pairs in length.

The length of the less stable intramolecular duplex is chosen so that formation of a target:probe intermolecular duplex is favoured so as to reduce the tendency of reformation of the hairpin duplex once the perfectly matched target has hybridized with the target-binding region of the probe. Usually, the complement of the target-binding region that enters into intramolecular hybridization with a portion of the target-binding region (i.e., region G in any of FIGS. 1A to 1D) is at least 4 bases in length. It is unlikely to be greater than fourteen bases in length. Preferably, the duplex portion of the hairpin containing a portion of the target-binding site is from four to ten bases in length, or between three and nine, between three and six or is four or is five bases in length.

It is also preferable that formation of the hairpin involving the target-binding region is generally favoured over the binding of the probe and a nucleic acid molecule having a sequence different from the target by one or more bases. Avoidance of hybridization with the probe of a molecule having a sequence matching the target-binding region by all but only one base can make the invention useful, for example in identifying a single nucleotide polymorphism. Parameters affecting the performance of such a probe include the length of the target-binding site, the length of the duplex portion of the hairpin (i.e., the E-G duplex of FIGS. 1A to 1D), the composition and specific sequence of each of these sites. This being said, in preferred embodiments, the target-binding region is most likely to be at least sixteen bases in length. It could be up to forty, more preferably up to 30, and more preferably up to twenty-five bases. The overall length of the target binding region is unlikely to be less than ten, and more preferably at least fifteen or twenty bases in length. The embodiment described herein, in which the target length is 24 bases, appears to be highly preferred, particularly in applications where a repertoire of probes is to be used together as a family of complements on tags of target molecules.

The general structure of preferred embodiment probes are shown in FIGS. 1A to 1D. All of these probes are anchored to a solid support, but the need for such anchoring is dependent upon the use to which the probe is being put.

An $HP^2$ hairpin comprises a structure A-B-C-D-E-F-G wherein:
A and C are nucleic acid sequences which are capable of hybridizing to each other to form an intramolecular duplex A:C;
B is a linker which covalently links A and C;
D is a single stranded nucleic acid sequence;
E and G are nucleic acid sequences which are capable of hybridizing to each other to form an intramolecular duplex E:G such that the E:G duplex is less stable than the A:C duplex;
F is a linker which covalently links E and G.

All of D is substantially complementary to a portion of the target sequence. A contiguous portion of at least one of D and F, together with the sequence of E make up a complete complement to the target sequence. Any portion of D or F that is complementary to the target sequence can act as a nucleation site. Of course, the longer such complementary portion, the more likely it is to act as a nucleation site.

The immobilized double hairpin has regions A and C, which are mutually complementary and form a highly stable intramolecular duplex (also referred to herein as a "stem"). Region D of the double hairpin probe is often the primary nucleation site and is flanked by region E, which is complementary to region G forming a second less stable intramolecular duplex. Under suitable conditions, upon nucleation of a target sequence to region D, intermolecular duplex formation is propagated while simultaneously disrupting intramolecular duplex E:G. Loop F is substantially complementary to the incoming target such that it may be a secondary nucleation site provided that the bases are accessible. The sequence of region G is dictated by the sequence of region E, to which it is complementary, but it is otherwise unrelated to the target sequence.

$HP^2$ embodiments of the invention include regions A-B-C-D-E-F-G, while HP-1 embodiments include regions D-E-F-G. See FIGS. 1C and 1D. The single hairpin structure of such a probe thus includes a portion of the target-binding sequence.

Figure 1B:
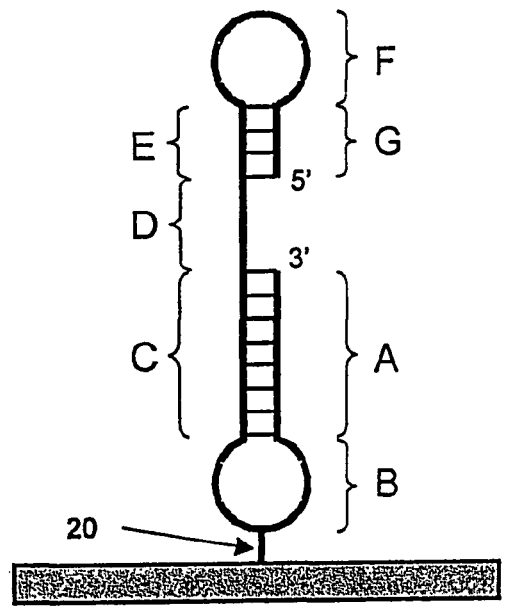

Loop B of the double hairpin is a member which covalently links the nucleic acid sequences A and C together and holds them in sufficiently close proximity to each other to permit formation of an A:C intramolecular duplex. Attachment to the solid phase occurs through modifications incorporated into a nucleotide of loop B. This attachment is illustrated in FIGS. 1A and 1B. In preferred embodiments, B covalently links A and C and is a nucleic acid sequence, but in other embodiments, B may not be a nucleic acid sequence.

In a particular preferred embodiment, region D of an $HP^2$ arrangement is substantially complementary to a terminal region of the nucleic acid molecule containing a target sequence. In the case of a FIG. 1A embodiment, this would be the 3'-end of the target molecule. In a FIG. 1B embodiment, this would be the 5;-end of the target molecule. With such an arrangement upon hybridization of the hairpin with a target nucleic acid sequence, a "nicked" duplex structure forms, comprising contiguous regions of intramolecular hairpin: hairpin duplex (A and C) and intermolecular target:hairpin duplex (D and target). This results in base stacking between the intramolecular duplex of the more stable hairpin and the intermolecular duplex (i.e., between a terminal base of the target sequence and a terminal base of the capture moiety) and provides greater sequence stringency than hybridization to a simple single strand, as described in Khrapko et al. (1991). DNA Sequencing Mapping 1:375-388. Also, as detailed below, the nicked duplex structure may include a duplex-binding-ligand binding site.

In HP² embodiments in which the target-probe hybrid is a nicked duplex, the target:capture moiety duplex contains a binding site for at least one duplex-binding ligand. A duplex-binding ligand is a moiety which binds duplex nucleic acids in preference to single strands. A preferred duplex-binding ligand recognizes (binds to) a recognition site (or binding site) of a duplex nucleic acid and binds thereto more strongly bound than it does to a non-recognition sites. These are referred to herein as "sequence-specific" duplex-binding ligands. Thus, in such a preferred embodiment, the target:capture moiety duplex comprises a binding site for a sequence-specific duplex-binding ligand. Other duplex-binding ligands do not exhibit site specificity and are referred to herein as "non-sequence-specific" duplex-binding ligands. Exemplary duplex-binding ligands include enzymes, such as restriction enzymes, polymerases, ligases, and the like; drugs such as actinomycin D; non-sequence-specific intercalaters such as ethidium bromide; and the like. In preferred embodiments, the duplex-binding ligand, whether sequence-specific or non-sequence-specific, does not covalently modify any duplex, e.g., does not create and/or cleave any covalent bond, e.g., a covalent bond of the capture moiety or the target nucleic acid. In preferred embodiments, the duplex-binding ligand is thus other than a ligase or a polymerase.

Where circumstances permit, i.e., where the terminal sequence of a target molecule is the complement of a target-binding sequence, it may be possible to design the capture moiety such that the terminal base of an intramolecular duplex-forming region, when taken in combination with a terminal base of the target strand, forms a binding site for a sequence specific duplex-binding ligand. In other words, the duplex-binding-ligand binding site includes the nick in the duplex formed by hybridization of the target to the capture moiety. For example, the duplex-binding-ligand Actinomycin D binds preferentially to the sequence 5'-AGCT-3'. Illustratively, the capture moiety can be chosen to have the 5'-terminal sequence 5'-CT- as part of an intramolecular duplex, and the target strand is selected to have the 3'-terminal sequence -AG-3'. Thus, upon hybridization of the target strand to the capture moiety, the nicked duplex 5'-AG-CT-3" is formed, wherein the "G-C" represents the nick between G and C. This embodiment will be useful when discrimination between target sequences of differing length (e.g., cut and uncut targets) are used. If the longer target sequence forms an overhang when hybridized to the hairpin capture moiety, addition of a duplex-binding-ligand which has a recognition site which includes the nick site will improve discrimination between cut and uncut target sequences. It may also find use in circumstances in which it is possible to design or select sequences to be used de novo, as a repertoire of tags (targets) and tag complements (tag sequence binding-site) of probes.

The capture moiety can also be selected so that a duplex-binding-ligand binding site will form upon probe-target hybridization so as not to include a nick, i.e., the duplex-binding-ligand binding site is internal of the target-probe duplex region. For example, the target sequence may be selected to contain the sequence 5'-AGCT-3'. Thus, the target-specific region of the hairpin capture moiety will contain the complementary sequence, and Actinomycin D will recognize the duplex formed upon binding of the target strand to the capture moiety. The presence of the duplex-binding-ligand cam increase the amount of target:capture moiety duplex which is formed (by binding the duplex), thereby improving sensitivity. The capture moiety can also be selected so that more than one duplex-binding-ligand binding site is formed upon binding of the target strand to the hairpin. The binding sites may be for a single duplex-binding ligand (for example, several actinomycin D binding sites), or for more than one ligand (e.g., an actinomycin D site and an EcoRI site). By adding the appropriate duplex-binding ligands, a desirable balance between detection sensitivity and target selectivity can be obtained.

It will also be recognized that duplex denaturing reagents can be used to increase the specificity of target binding to the capture moiety. In other words, a duplex denaturant can be used to destabilize duplex formation, particularly duplexes resulting from hybridization of mismatched nucleic acid sequences. Duplex denaturants include any means of favoring single strand formation and disfavoring duplex formation. Increased temperature (heating) may be used as a duplex denaturant, although this is not preferred. In certain embodiments, a duplex denaturant is a chemical or biochemical reagent. Exemplary duplex denaturants include enzymes and proteins such as single-strand binding protein (e.g., from *E. coli*), the G-5 protein, the gene 32 protein, Rec A, and helicases, as well as chemical denaturants such as urea. Duplex denaturants can be identified by measuring the $T_m$ of a duplex in the presence and the absence of a suspected duplex denaturant; a duplex denaturant will lower the $T_m$. Preferred duplex denaturants do not have an adverse effect on other components of a reaction mixture, when used in amounts sufficient to destabilize at least one duplex. For example, a duplex denaturant should not inhibit the activity of enzymes, such as polymerase or ligase, if activity of such enzymes is desired.

If the duplex-binding ligand is also a duplex-modifying reagent (e.g., a restriction enzyme, a ligase, and the like) other methods of detection are possible. For example, contacting a target:capture moiety duplex with a duplex modifying agent such as a duplex-selective restriction enzyme can result in selective modification of the duplex, but no modification of the unbound target or unbound capture moiety. With an appropriate choice of target and capture moiety, the target is detected by detecting modification of the capture moiety or the target sequence. In an exemplary embodiment, the capture moiety is labelled with a detectable label such as are known in the art, and a target strand is hybridized to the capture moiety. The target:capture moiety intermolecular duplex thus formed is then cleaved by a restriction enzyme. Detection of the labelled fragments of the capture moiety would thereby detect the presence of the target sequence of interest.

As already mentioned, in certain embodiments, a probe of the invention is derivatized to allow binding to a solid support. Many methods of derivatizing a nucleic acid for binding to a solid support are known in the art. The capture moiety may be bound to a solid support through covalent or non-covalent bonds. In a preferred embodiment, the nucleic acid capture moiety is covalently bound to biotin to form a biotinylated conjugate. The biotinylated conjugate is then bound to a solid surface, for example, by binding to a solid, insoluble support derivatized with avidin or streptavidin. In an HP² arrangement, the capture moiety can be conveniently derivatized for binding to a solid support by incorporating modified nucleic acids in the loop region of the more stable hairpin.

Thus, in a particular embodiment, the capture moiety is derivatized in the loop region of the more stable intramolecular duplex to permit binding of an HP² type probe to a solid support. For example, biotin-modified nucleic acids can be incorporated into the loop region to permit binding to a streptavidin-coated solid support. Coating of surfaces with streptavidin has been described in, for example, U.S. Pat. No. 5,374,524 to Miller. As noted above, a variety of moieties useful for binding to a solid support (e.g., biotin, antibodies, and the like), and methods for attaching them to nucleic acids, are known in the art.

In particular embodiments, the solid support is a glass slide, a bead, or a microtitre well. Use of beads allows the derivatized nucleic acid capture moiety to be separated from a reaction mixture by centrifugation or filtration, or, in the case of magnetic beads, by application of a magnetic field. Use of multiwell plates allows simultaneous screening for multiple target sequences using multiple double hairpins, and also allows the use of automated equipment to perform the screening assays. In certain embodiments, as for microarray-based platforms, it may be desired to use multiple probes of the invention to detect a plurality of target sequences. In such embodiments that include an HP$^2$ type probe, it may be found to be advantageous to use a family of probes in which the more stable hairpins are the same as each other, from probe to probe.

As for linear loop embodiments, linkage to a solid support is accomplished by the same means as described for the HP$^2$ embodiments. Usually, but not necessarily, the linkage to the support would be via the terminal nucleotide, i.e., the free end of the probe at D.

It is possible, with all type embodiments to have the linkage in region G, or in region F, as exemplified further in Example 6.

It is less likely that a linkage base would be included within the target binding site of a probe, as this could interfere with proper probe-target hybridization.

Methods of the invention include detecting both natural and non-natural nucleic acid sequences. For example, methods of the invention are used to detect nucleic acid sequences from the genome of an organism. In other embodiments, methods of the invention are used to detect the products of nucleic acid reactions such as strand cleavage, ligation, extension, modification, and the like. Thus, the methods of the invention can be used to detect nucleic acid sequences directly, by hybridization, or indirectly, by detection of amplification products from, for example, amplification products from polymerase chain reaction or ligase chain reaction. The methods of the invention can also be used to detect and discriminate a specific nucleic acid sequence which varies from a second nucleic acid sequence by as little as one base, although greater differences are likely to improve results obtained using probes of the invention. In addition, methods and compositions of the invention can be used for detecting and discriminating a specific nucleic acid sequence which varies from one or more other nucleic acid sequences by two bases, three bases, or more.

There are various kits according to this invention, described elsewhere. A kit of the present invention is any combination of physical elements that could be used to conduct a method of the invention. A kit can also include instructions for carrying a method of the invention. A capture moiety of a kit may be derivatized and ready to be immobilized and hybridized or hybridized then immobilized in solution. Kits may also include assay reagents, e.g., salts, buffers, nuclease inhibitors, restriction enzymes, denaturants, a detection system for detecting the presence or absence of hybridization of the target nucleic acid and the nucleic acid capture moiety, a sequence-specific duplex-binding ligand, a non-sequence-specific duplex-binding ligand, a duplex-binding ligand which does not create or cleave any covalent bond, a duplex denaturant, instructions for use. Kits may include a target or model target for a positive control test, and a "sample" without a target for a negative control test.

In another aspect, the invention features a reaction mixture. In preferred embodiments, the reaction mixture includes one or more of the following: an immobilized nucleic acid capture moiety of the invention, a solid or insoluble support, a non-immobilized nucleic acid capture moiety of the invention, a target nucleic acid strand, a sequence-specific duplex-binding ligand, a non-sequence-specific duplex-binding ligand, a duplex-binding ligand which does not create or cleave any covalent bond, a duplex denaturant, a standard. In preferred embodiments, the reaction mixture is a solution.

While methods of the invention are easily performed manually, they are readily adapted for use with automated equipment. For example, robotic workstations are available which are capable of performing multiple analyses in parallel through the use of automated pipetting and automated plate readers for use with multi-well plates. Thus, in a preferred embodiment, the methods of the invention are performed with automated equipment. The use of automated equipment allows rapid, inexpensive analysis of single or multiple samples, for one or more target nucleic acid sequences.

EXAMPLE 1

Probes having SEQ ID NOs:1 and 2 (Table 1) were tested to determine their relative abilities in discriminating between molecules having SEQ ID NOs:3 to 13 (Table 1).

Figure 2A:
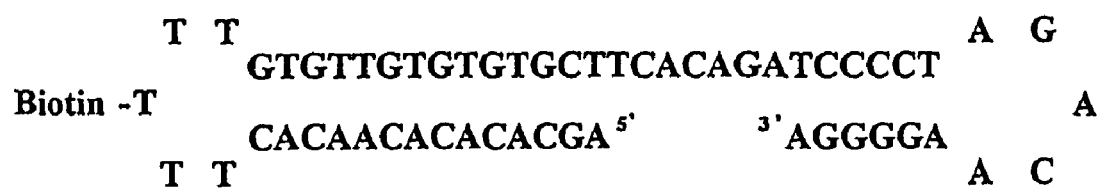
FIG. 2A shows a hairpin structure formed by the nucleotides 3-59 of SEQ ID NO: 1, the particular $HP^2$ capture probe used in Example 1.

The structure of the probe having SEQ ID NO:1 is shown schematically in FIG. 1A, and in greater detail in FIG. 2A. The probe has two hairpins. The duplex of the first hairpin (regions A and C in FIG. 1A) contains sixteen base pairs and the paired regions are linked by five thymidine residues (region B in FIG. 1A). The central thymidine is biotinylated and forms a link 20 to solid support 22. The remainder of the probe corresponds to regions D-E-F-G of the FIG. 1A schematic. The duplex region of the second hairpin is six base pairs in length (regions E and G of FIG. 1A). The target-binding sequence (D-E-F of FIG. 1A) is sixteen bases in length. The first hairpin is relatively stable in comparison to the second hairpin based on a comparison of calculated $T_m$ values for the sixteen base-pair stem (more stable duplex) and the six base-pair duplex (target end duplex).

Figure 2B:
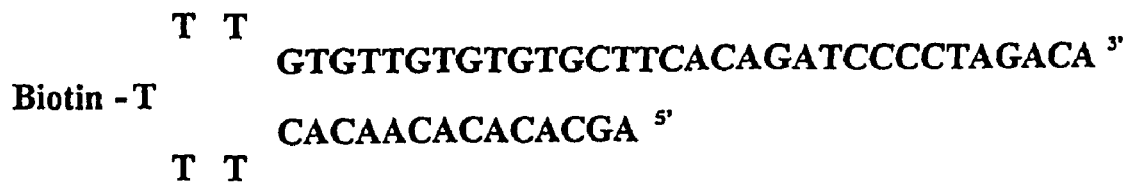
FIG. 2B shows a hairpin structure formed by nucleotides 3-53 of SEQ ID NO: 2, the second capture probe used in Example 1. The probe lacks a region "G", complementary to "E", and so the target binding-region of the probe does not form a hairpin.

The structure of the probe having SEQ ID NO:2 is shown in FIG. 2B. The six bases of the 3'-terminus of the probe, AAAAAA, are not sufficiently complementary with any other region of the probe to hybridize and form a second duplex. This probe thus lacks the second hairpin present in the probe having SEQ ID NO:1, but the remainder of the probe sequence is identical to that of SEQ ID NO:1.

A perfectly matched target sequence for each of the probes contains SEQ ID NO:3 (Table 1). Each of the remaining SEQ ID NOs:4 to 13 varies from SEQ ID NO:3 by one base. Each of these remaining molecules thus contains a sequence that is complementary to all but one of the bases in the target binding region of each of the probes. See Table 1, wherein the variant bases within the probes are in boldface. (It is to be noted that all target sequences shown in Table 1 are written in the 3'-5' direction for ease of visualization of duplex formation.)

All oligos were synthesized by Integrated DNA Technologies (IDT, Coralville, Iowa) using standard protocols and purified using polyacrylamide gel electrophoresis. Hairpin probes were biotinylated via the central thymidine of loop B to allow for attachment to avidin-coated microtitre wells. The 16 mer targets (SEQ ID NOs:3 to 13) were synthesized with a 5' FITC (fluorscein isothiocyanate) to allow for subsequent detection using an indirect chemiluminescent reaction.

Figure 3:
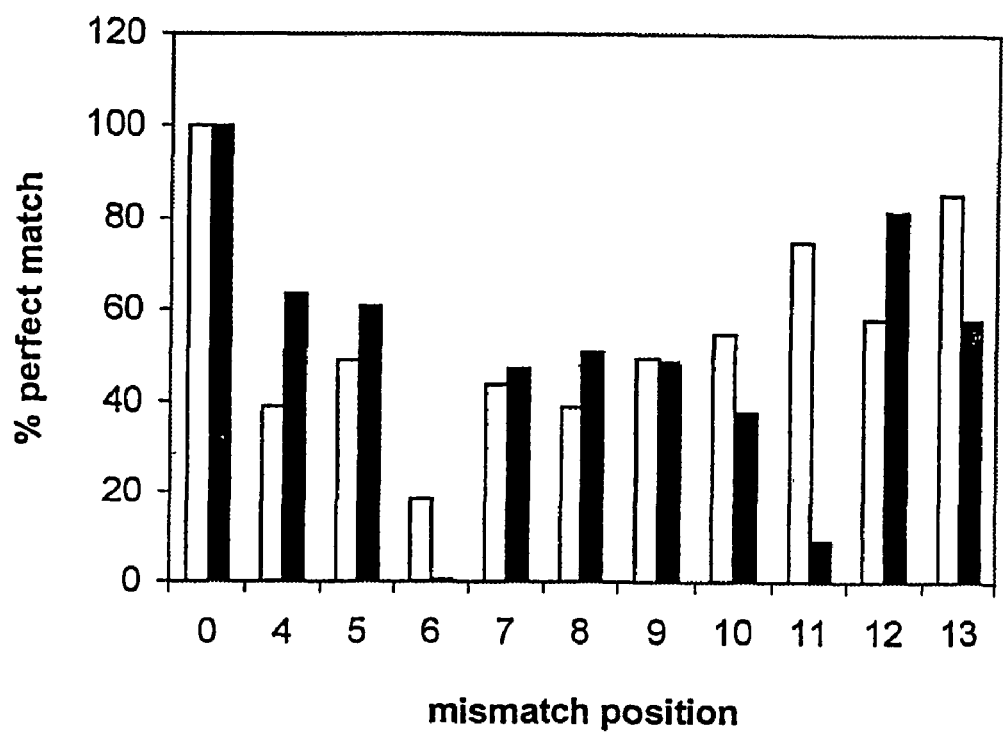
FIG. 3 is a bar graph showing relative hybridizations of different nucleic acid molecules with the capture probes of FIG. 2A (dark bars; SEQ ID NO:1) and 2B (light bars; SEQ ID NO:2) as described in Example 1. The percent hybridization of a nucleic acid sequence having a mismatch with the target-binding region of a probe with respect to the perfectly matched nucleic acid sequence with that probe (first two bars) is plotted for each nucleic acid sequence. The position of mismatch between a given target and the probe (as numbered in the target reading the 3'-5' direction) is given along the x-axis, the first pair of bars being for the matching probe:target combinations.

White, opaque, flat-bottom microtitre wells (Costar) were first coated using 100 µL of 0.2 µmol/L avidin in carbonate buffer (0.05 M carbonate/bicarbonate pH 9.6). Following a one hour incubation at room temperature, the wells were washed 6× in assay buffer (1M NaCl, 0.1M Tris, 0.08% Triton X-100, pH 8.0) using the Dynex 96-pin automated washer. Each probe was diluted in assay buffer to a final concentration of 0.05 µmol/L. One hundred microliters of each probe were then added to the avidin-coated wells (5 pmol/well), incubated for 30 minutes at room temperature while shaking and washed 6× using assay buffer. The matched target (SEQ ID NO. 3) and each of the ten different mismatched targets (SEQ ID NO. 4 to 13) were separately diluted in assay buffer to a final concentration of 0.5 nmol/L and 100 µL of each dilution were added to both the control and HP$^2$ probe-coated wells (0.05 pmol/well). Following a one hour incubation at room temperature with continuous shaking, the wells were washed 6× with assay buffer as described previously. An antibody-alkaline phosphatase conjugate specific for the FITC moiety present on the targets was diluted 5000× in antibody binding buffer (0.2M NaCl, 0.1M Tris, Triton X-100 (0.08%), pH 8.0) and 100 µL of the solution was added to each well and allowed to incubate for 30 minutes at room temperature with shaking. The wells were washed 6× using the antibody binding buffer. All wells were then equilibrated for the chemiluminescent reaction by adding 200 µL of substrate buffer (0.1M NaCl, 0.1M Tris, pH 9.5) and incubating for 5 minutes at room temperature. The buffer was then aspirated and 100 µL of CDP-Star substrate (Roche Molecular Diagnostics), diluted 100× in substrate buffer, was added to each well. The reaction was allowed to proceed for 5 minutes after which the plates were read using the Dynex MLX luminometer (Chantilly, Va., U.S.A). The results obtained are shown in FIG. 3. If an arbitrary cut-off signal equal to 10% of that generated by a perfectly matched hybrid is set as the maximum allowable limit required for discrimination, then the results indicate that the probe having a double hairpin, HP$^2$, (black bars) was able to effectively discriminate targets having SEQ ID NOs:6 and 11, corresponding to mismatch positions 6 and 11, respectively, relative to the 3'-end of the target. The positions of the mismatches for targets with SEQ ID NO. 6 and 11 correspond to the terminal base pairs on either side of the short duplex of HP$^2$.

TABLE 1

Oligonucleotide Sequences used in Examples 1, 2 and 3

| ID NO | Type | Sequence | |
|---|---|---|---|
| 1 | Probe | 5'-GAAGCACACACAACACTTTTTGTGTTGTGTGTGCTTC ACAGATCCCCTAGACA AGGGGA-3' | |
| 2 | Probe | 5'-GAAGCACACACAACACTTTTTGTGTTGTGTGTGCTTC ACAGATCCCCTAGACA AAAAAA-3' | |
| 3 | target | 3'-TGTCTAGGGGATCTGT-5' | |
| 4 | target | 3'-TGTGTAGGGGATCTGT-5' | (a) |
| 5 | target | 3'-TGTCAGGGGATCTGT-5' | (a) |
| 6 | target | 3'-TGTCTGGGGATCTGT-5' | (a) |
| 7 | target | 3'-TGTCTAAGGGATCTGT-5' | (a) |
| 8 | target | 3'-TGTCTAGAGGATCTGT-5' | (a) |
| 9 | target | 3'-TGTCTAGGAGATCTGT-5' | (a) |
| 10 | target | 3'-TGTCTAGGGAATCTGT-5' | (a) |
| 11 | target | 3'-TGTCTAGGGGGTCTGT-5' | (a) |
| 12 | target | 3'-TGTCTAGGGGAACTGT-5' | (a) |
| 13 | target | 3'-TGTCTAGGGGATGTGT-5' | (a) |
| 14 | probe | 5'-TTGTGTTGTGTGTGCTTC ACAGATCCCCTAGACA AGGGGA-3' | |
| 15 | probe | 5'-GAAGCACACACAACACTTTTTGTGTTGTGTGTGCTTC ACTGATCCCCTAGTCA AGGGGA-3' | |
| 16 | probe | 5'-GAAGCACACACAACACTTTTTGTGTTGTGTGTGCTTC ACTGATCCCCTAGTCA AAAAAA-3' | |
| 17 | target | 3'-TGACTAGGGGATCAGT-5' | |

(a) The position within the target that is mismatched with respect to each of the probes having SEQ ID NOs:1, 2 and 14 is in boldface and the positions within the target that are mismatched with respect to the probes having SEQ ID NOs:15 and 16 are underlined.

EXAMPLE 2

In this example, probes having SEQ ID NOs:1 and 14 (Table 1) were tested to determine their relative abilities in discriminating between molecules that have SEQ ID NOs:6 to 11 (Table 1).

The structure of the probe having SEQ ID NO:1 is shown schematically in FIG. 1A and in greater detail in FIG. 2A, and its various features are described in Example 1.

Figure 1C:
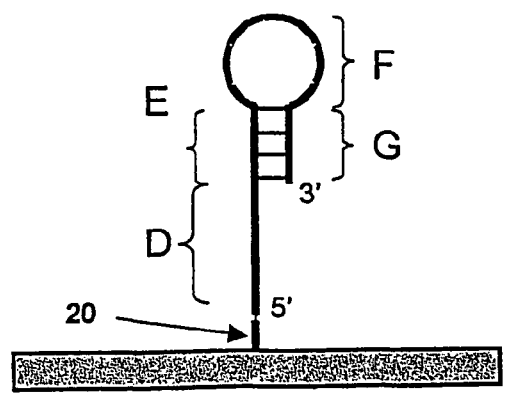
Figure 1D:
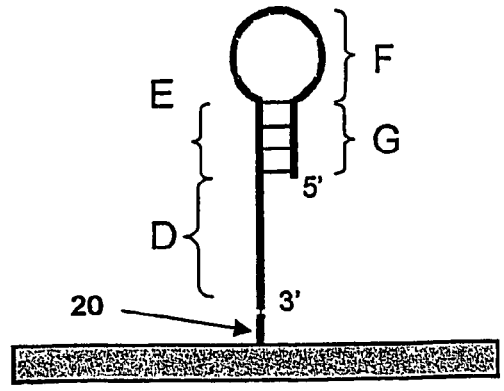

The structure of the probe having SEQ ID NO:14 is similar to the schematic shown in FIG. 1C. It is similar to the probe having SEQ ID NO:1, but is lacking the first 19 bases, corresponding to region A and three bases of B of SEQ ID NO:1. This probe thus includes region C-D-E-F-G and does not have a hairpin at its 5'-end. Two additional 5'-terminal thymidines, one of which is biotinylated for anchoring to a solid support.

The protocol outlined in Example 1 was followed with probes having SEQ ID NOs:1 and 14 with targets having SEQ ID NOs:3 and 6 to 11. The results are shown in FIG. 4. In this case, net RLUs (relative light units) are plotted for each target and probe combination tested.

Figure 4A:
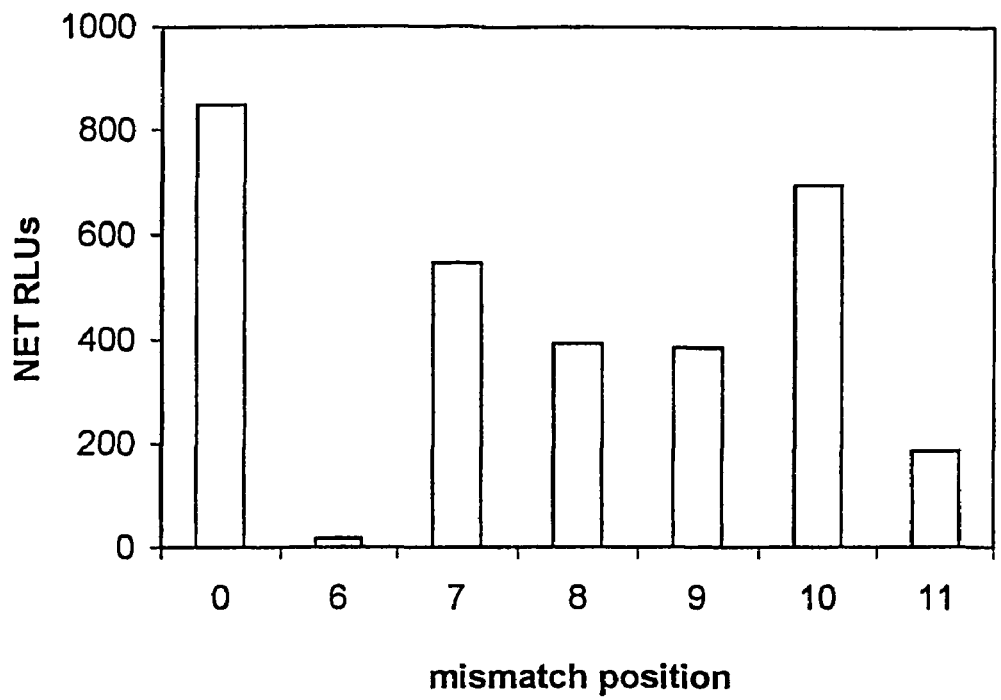
FIG. 4A is a bar graph showing relative hybridizations of different nucleic acid molecules, SEQ ID NOs:3 and 6 to 11, with the capture probe having SEQ ID NO:1
Figure 4B:
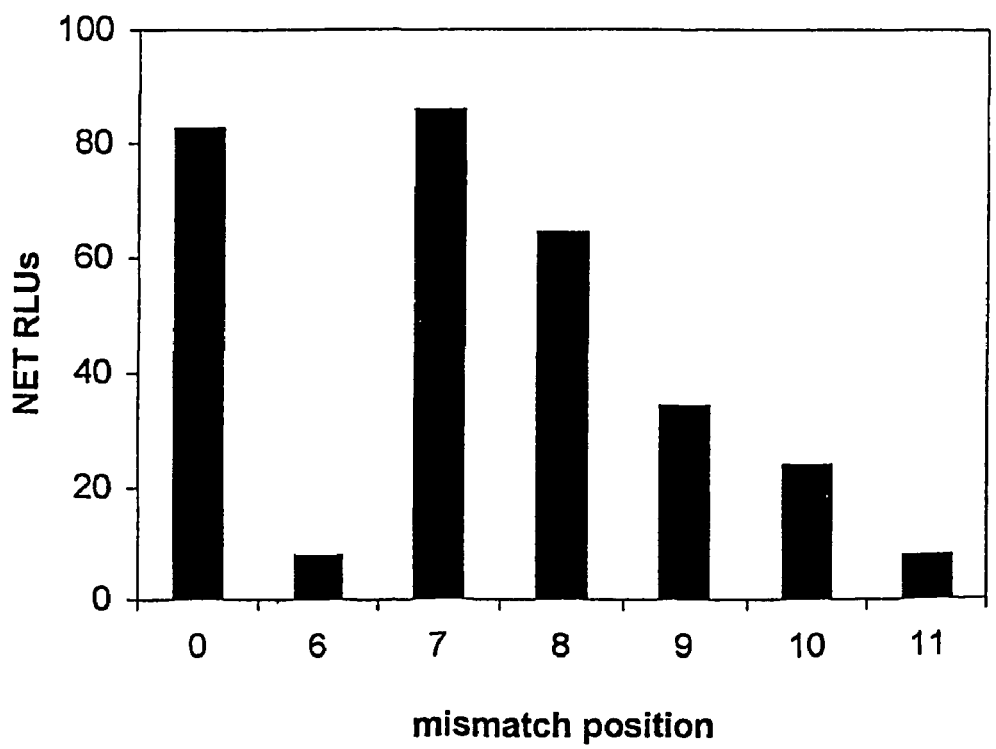
FIG. 4B is a bar graph showing relative hybridizations of the nucleic molecules with the capture probe having SEQ ID NO:14 See Example 2. In each case, the position of mismatch between a given target and the probe (as numbered in the target reading in the 3'-5' direction) is given along the x-axis, each of the first bars being for the matching probe:target combination. Net Relative Light Units (RLUs) for each probe-nucleic acid sequence is shown on the on the y-axis.

It can be seen that the intensity of the results obtained with the probe lacking the first hairpin (FIG. 4B) are generally much lower than the intensity of the results obtained with the double-hairpin probe (FIG. 4A). This indicates that the sensitivity of a system using the double hairpin probe should be substantially greater than the sensitivity of an assay using a comparable probe lacking the 5'-hairpin.

EXAMPLE 3

Probes having SEQ ID NOs:15 and 16 (Table 1) were tested to determine their relative abilities in discriminating between molecules having SEQ ID NOs:4 to 13 and 17 (Table 1).

to 13 and 17) was added such to a final concentration of 0.5 pmol/well as opposed to the 0.05 pmol/well quantity added in Examples 1 and 2. The results are shown in FIG. 5 in which the percent intensity of each mismatched target-probe relative to the perfect match-probe combination is shown for each target-probe combination.

Figure 5:
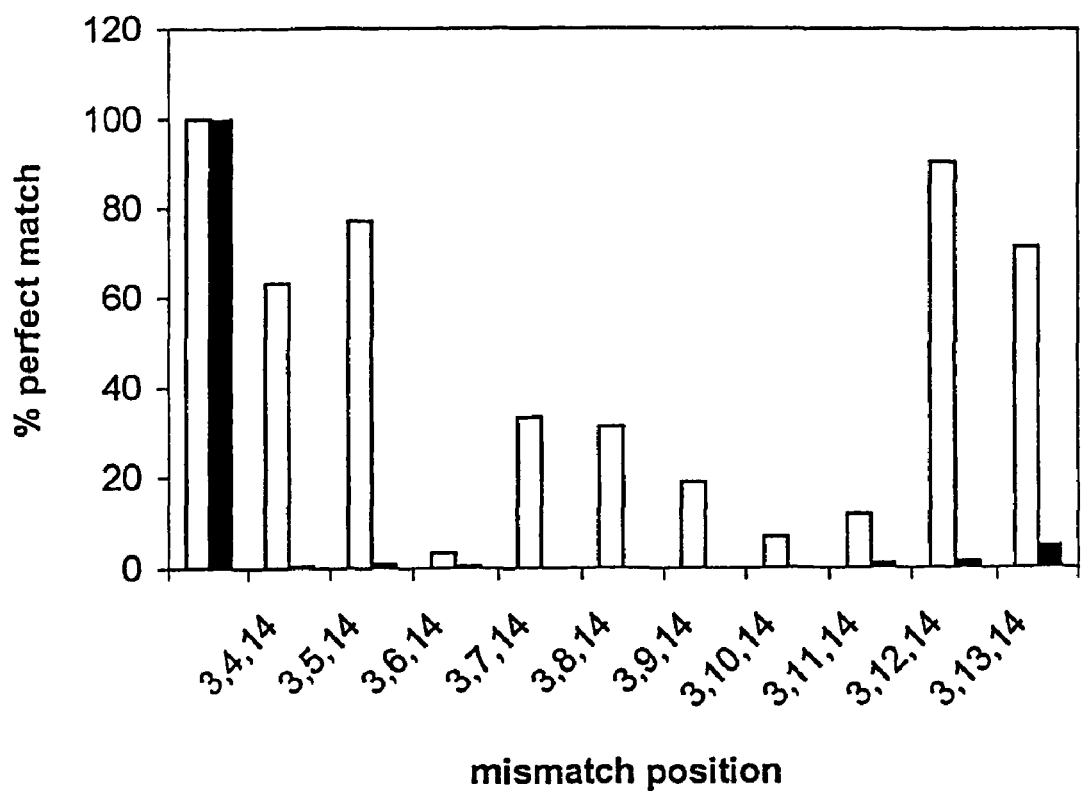
FIG. 5 is a bar graph showing relative hybridizations of different nucleic acid molecules with the capture probes having SEQ ID NO:15 (dark bars) and SEQ ID NO:16 (light bars) as described in Example 3. The percent hybridization of a nucleic acid sequence having a mismatch (identified on the x-axis by SEQ ID NO) with each probe is plotted for each nucleic acid sequence. The positions of mismatch between a given target and the probe (as numbered in the target reading in the 3'-5' direction) is given along the x-axis, the first pair of bars being for the matching probe:target combinations.

It can be seen from FIG. 5 that the intensity of each mismatch and the $HP^2$ probe (SEQ ID NO:15; black bars) combination is less than 10% the intensity of the perfect match and $HP^2$ probe. Applying the 10% criterion to the results obtained with the probe lacking the 3'-hairpin probe (white bars), only two of the mismatching targets (SEQ ID NOs:6 and 10) were found to be discriminated from the perfect match-probe combination.

TABLE 2

Oligonucleotide Sequences used in Examples 4 and 5

| ID NO | | | |
|---|---|---|---|
| | | Double Hairpin Probe (FIG. 7): | |
| 18 | | 5'-CTATACCACACCTTTTTGGTGTGGTATAG TGATTGTATTGAGATTTGATTGTA AAATCTCAAT-3' x | |
| | | Single 5'-Hairpin Probe (FIG. 7): | |
| 19 | | 5'-CTATACCACACCTTTTTGGTGTGGTATAG TGATTGTATTGAGATTTGATTGTA-3' x | |
| | | Targets: | |
| 20 | | Match | 3'-ACTAACATAACTCTAAACTAACAT-5' |
| 21 | (4a) | Mismatch | 3'-ACTAACATAACTCTAACATATTTC-5' |
| 22 | (4b) | Mismatch | 3'-CATAACATAACTCTAAACTATTTC-5' |
| 23 | (4c) | Mismatch | 3'-CATATTTCAACTCTAAACTAACAT-5' |
| 24 | (3a) | Mismatch | 3'-ACTAACATAACTCATAACTATTTC-5' |
| 25 | (3b) | Mismatch | 3'-ACTAACATAACTCATATTTCACAT-5' |
| 26 | (3c) | Mismatch | 3'-CATAACATAACTCTAATTTCACAT-5' |
| 27 | (3d) | Mismatch | 3'-ACTACATAAACTCTAAACTATTTC-5' |
| 28 | (3e) | Mismatch | 3'-TTTCACATCATACTAAACTAACAT-5' |
| 29 | (3f) | Mismatch | 3'-ACTACATATTTCCTAAACTAACAT-5' |
| 30 | (2a) | Mismatch | 3'-ACTAACATCATACTAAACTATTTC-5' |
| 31 | (2b) | Mismatch | 3'-ACTAACATCATATTTCACTAACAT-5' |
| 32 | (2c) | Mismatch | 3'-TTTCACATAACTCATAACTAACAT-5' |
| 33 | (2d) | Mismatch | 3'-ACTACATAAACTCTAATTTCACAT-5' |
| | | Single 3'-Hairpin Probe (FIG. 9): | |
| 34 | | | 5'-TGATTGTATTGAGATTTGATTGTA AAATCTCAAT-3' x |
| | | Linear Probe (FIG. 9): | |
| 35 | | | 5'-TGATTGTATTGAGATTTGATTGTA-3' x |

Probes having SEQ ID NOs:15 and 16 have the same sequences as probes having SEQ ID NOs:1 and 2, respectively, except that the third and fourteenth bases of the target-binding sequence have each been changed from A to T. This means that each of the nucleic acid molecules having SEQ ID NOs:4 to 13 contain three mismatches with respect to the probes having SEQ ID NOs:15 and 16. SEQ ID 1) NO:17 is the matching complement to the target-binding sequence of these probes. The percent identity between the perfect match and each of molecules having SEQ ID NOs:4 to 13 is thus $13/16=81.25\%$.

The protocol outlined in Example 1 was again followed, except that in this case each target molecule (SEQ ID NOs:4

EXAMPLE 4

Probes having SEQ ID NOs:18 and 19 (Table 2) were tested to determine their relative abilities in discriminating between molecules having SEQ ID NOs:20 to 33.

Probe having SEQ ID NO:18 has a general structure similar to that of the probe having SEQ ID NO:1 in Example 1 in that it is capable of forming a double-hairpin ($HP^2$) arrangement. The probe having SEQ ID NO:19, like SEQ ID NO:2 in Example 1, forms a single hairpin, at its 5'-end, and the remaining sequence at the 3'-end of the molecule, containing the target-binding region does not contain a sequence that should form a hairpin.

Figure 6:
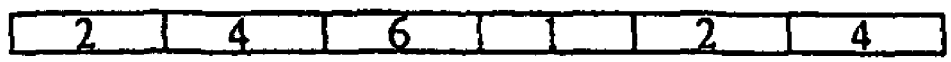
FIG. 6 is a schematic representation showing block arrangements of a probe target-binding sequence (top row), its complementary sequence (second row) and thirteen mis-matching sequences, described in Example 4.
Figure 6:
Figure 6:
Figure 6:
Figure 6:
Figure 6:
Figure 6:
Figure 6:
Figure 6:
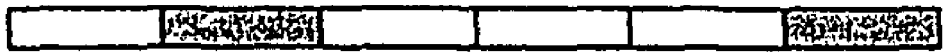
Figure 6:
Figure 6:
Figure 6:
Figure 6:
Figure 6:
Figure 6:

The target-binding regions sequences of the probes having SEQ ID NOs:18 and 19 are identical to each other. As seen on Table 2, the target-binding region is 24 bases in length. Experiments were conducted with targets containing nucleic acid sequences each of which has at least ⅔ identity with the perfectly matching target sequence, when in compared in perfect end-to-end alignment. The perfect complement to the target binding sequence (SEQ ED NO:20) and thirteen mismatching targets, having SEQ ID NOs:21 to 33 shown in Table 2, were used. Each 24-mer sequence can be thought of as being a string of six 4-mer blocks. Mismatched targets were designed such that the identities of four blocks between any given mismatch target are complementary to corresponding blocks of the target-binding region. A schematic representation of the sequences is shown in FIG. 6. As can be seen, since four out of six blocks of any given target are complementary with four blocks of the target-binding region, each such pair will have at least ⁴⁄₆, i.e., 66⅔ percent, homology with each other. The precise degree of homology depends upon the 4-mer sequences actually used in constructing the molecules.

Figure 7:
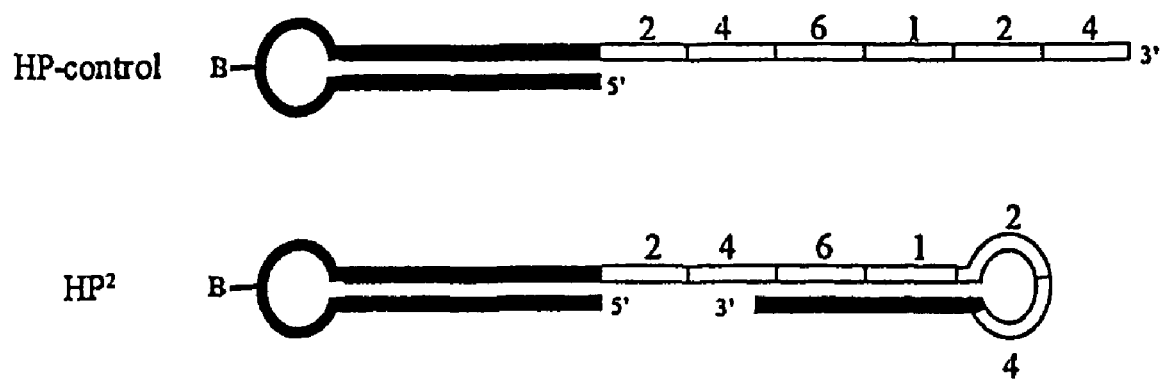
FIG. 7 is a schematic diagram, showing the block arrangement of sequences, as numbered in the top row of FIG. 6, of the two probes described in Example 4. The upper diagram illustrates the probe having a single hairpin at its non-target end. The lower diagram illustrates the probe having a hairpin at both ends.

The arrangement of the blocks of the target-binding region of probes used in the experiments is shown schematically in FIG. 7 and the full sequences are shown as SEQ ID NOs:18 and 19 in Table 2. From FIG. 7 it can be seen that the double hairpin probe (SEQ ID NO:18) has two single stranded regions within the target-binding region of the probe. The first of these single stranded regions is made up of bases 1 to 7 of the target-binding region, numbering the bases 1 to 24 in the 5'-3' direction. One can thus see that the duplex formed upon internal hybridization of the 3'-end of the double hairpin begins at the eighth base of the target-binding sequence. The internal duplex extends to the 17th base of the probe and a second single stranded region extends between the 18th and 24th bases. In terms of the schematic shown in FIG. 1A, it can thus be said that region A-B-C consists of the first 29 bases of SEQ ID NO:18; region D consists of the next seven bases; region E consists of the next ten bases; region F consists of the next seven bases; and region G consists of the final ten bases.

The probe having sequence SEQ ID NO:19 includes region A-B-C-D-E-F of the probe having SEQ ID NO:18. Lacking region G, this probe lacks a hairpin at the 3'-end of the molecule.

All oligos were synthesized by Integrated DNA Technologies (IDT, Coralville, Iowa) using standard protocols and purified using polyacrylamide gel electrophoresis. Probes were biotinylated via the central thymidine of loop B to permit attachment to avidin-coated microtitre wells. Each 24-mer target was synthesized with a 5' FITC moiety to allow for subsequent detection using an indirect chemiluminescent reaction.

Figure 8:
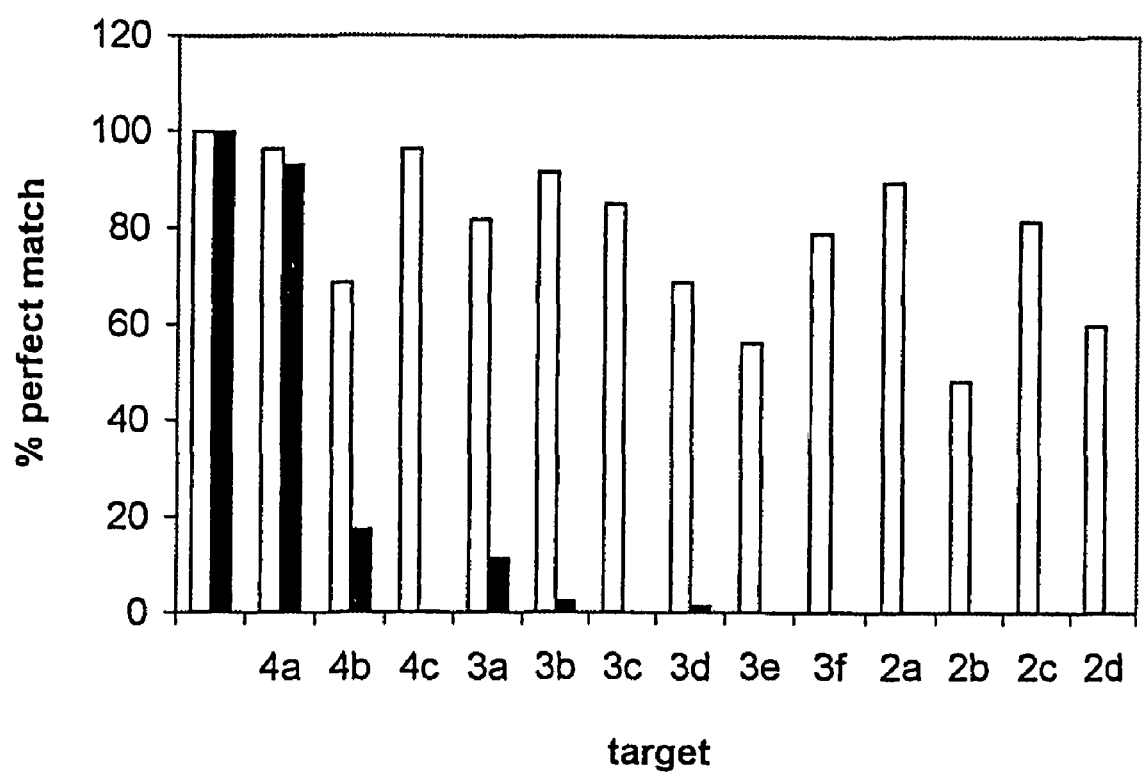
FIG. 8 is a bar graph showing relative hybridizations of different nucleic acid molecules with the capture probes having SEQ ID NO:18 (dark bars) and SEQ ID NO:19 (light bars) as described in Example 4. The percent hybridization of a nucleic acid sequence having a mismatch with each probe is plotted for each nucleic acid sequence, identified by the identifier given in FIG. 6 and Table 2, the first pair of bars being for the matching probe:target combinations.

White, opaque, flat-bottom microtitre wells (Costar) were first coated using 100 μL of 0.2 μmol/L avidin in carbonate buffer (0.05 M carbonate/bicarbonate pH 9.6). Following a one hour incubation at room temperature, the wells were washed 6× in assay buffer (1M NaCl, 0.1M Tris, 0.08% Triton X-100, pH 8.0) using a Dynex 96-pin automated washer. All probes were diluted in assay buffer to a final concentration of 0.05 μmol/L. One hundred microliters of each probe (5 pmol/well) were then added to the avidin-coated wells, incubated for 30 minutes at room temperature while shaking and washed 6× using assay buffer. The matched target together with the 13 different mismatched targets were individually diluted in assay buffer to a final concentration of 25 nmol/L and 100 μL of each dilution were added to all probe-coated wells (2.5 pmol target/well). Following a one hour incubation at 42° C. with continuous shaking, the wells were washed 6× with assay buffer as described above. An antibody-alkaline phosphatase conjugate specific for the FITC moiety present on the hybridized targets was diluted 2000× in antibody binding buffer (0.2M NaCl, 0.1M Tris, Triton X-100, pH 8.0) and 100 μL of the solution was added to each well and allowed to incubate for 30 minutes at room temperature with shaking. The wells were washed 6× using the antibody binding buffer. All wells were then equilibrated for the chemiluminescent reaction by adding 200 μL of substrate buffer (0.1M NaCl, 0.1M Tris, pH 9.5) and incubating for 5 minutes at room temperature. The buffer was then aspirated and 100 μL of CDP-Star substrate (Roche Molecular Diagnostics), diluted 100× in substrate buffer, were added to each well. The reaction was allowed to proceed for 5 minutes after which the plates were read using the Dynex MXL luminometer (Chantilly, Va.). The results obtained are presented in FIG. 8.

As can be seen, the double hairpin probe (SEQ ID NO:18; black bars) was able to discriminate ten of the thirteen mismatched targets when the arbitrary 10% of perfect match intensity previously described was used as a cutoff point. The probe having SEQ ID NO:19 (white bars), lacking a hairpin at the target-binding end of the molecule (3'-end), did not discriminate any of the thirteen mismatched targets from the perfect match using this criterion.

EXAMPLE 5

Figure 9:
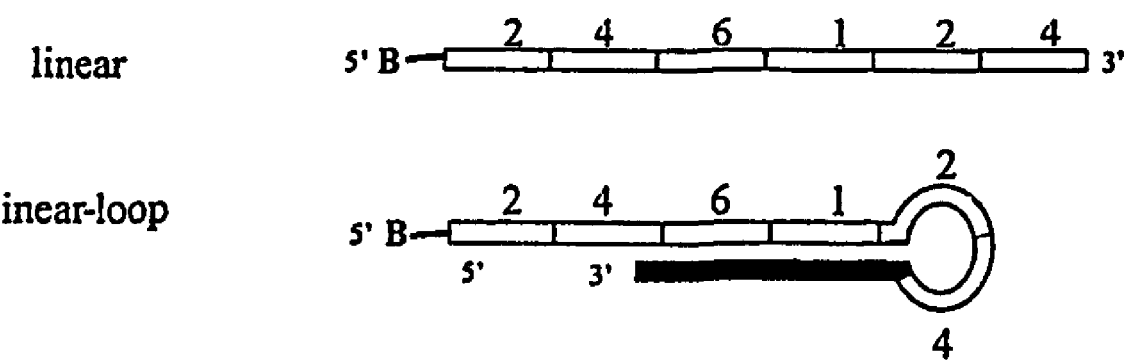
FIG. 9 is a schematic diagram, showing the block arrangement of sequences, as numbered in the top row of FIG. 6, of the two probes described in Example 5. The upper diagram illustrates the probe having no hairpin. The lower diagram illustrates the probe having a hairpin at its target-binding (3'-) end.

Probes having SEQ ID NOs:34 and 35 (Table 2) were tested to determine their relative abilities in discriminating between molecules having SEQ ID NOs:20 to 33 (Table 2). The sequence of the target-binding region of each of these probes is the same as that for each of the probes described in Example 4, and their general structures in terms of the blocks described in Example 4 are shown in FIG. 9.

The probe having SEQ ID NO:34 has the general structure of the probe illustrated in FIG. 1C. The probe thus includes region D-E-F-G, E and G being complementary and spaced from each other so to be capable of hybridizing with each other to form the duplex of a hairpin Region D-E-F-G of the probe having SEQ ID NO:34 has the same nucleic acid sequence as the corresponding region of SEQ ID NO:18 described in Example 4. Lacking region A-B-C, this probe does not have a hairpin at the anchor end, i.e., 5'-end of the molecule.

The probe having SEQ ID NO:35 includes region D-E-F of the probe having SEQ ID NO:34. Lacking regions A-B-C and G, this probe does not have a hairpin at either end of the molecule.

The relationship between the target-binding site and the various target test sequences (SEQ ID NOs:20 to 33) are shown in Table 2.

Figure 10:
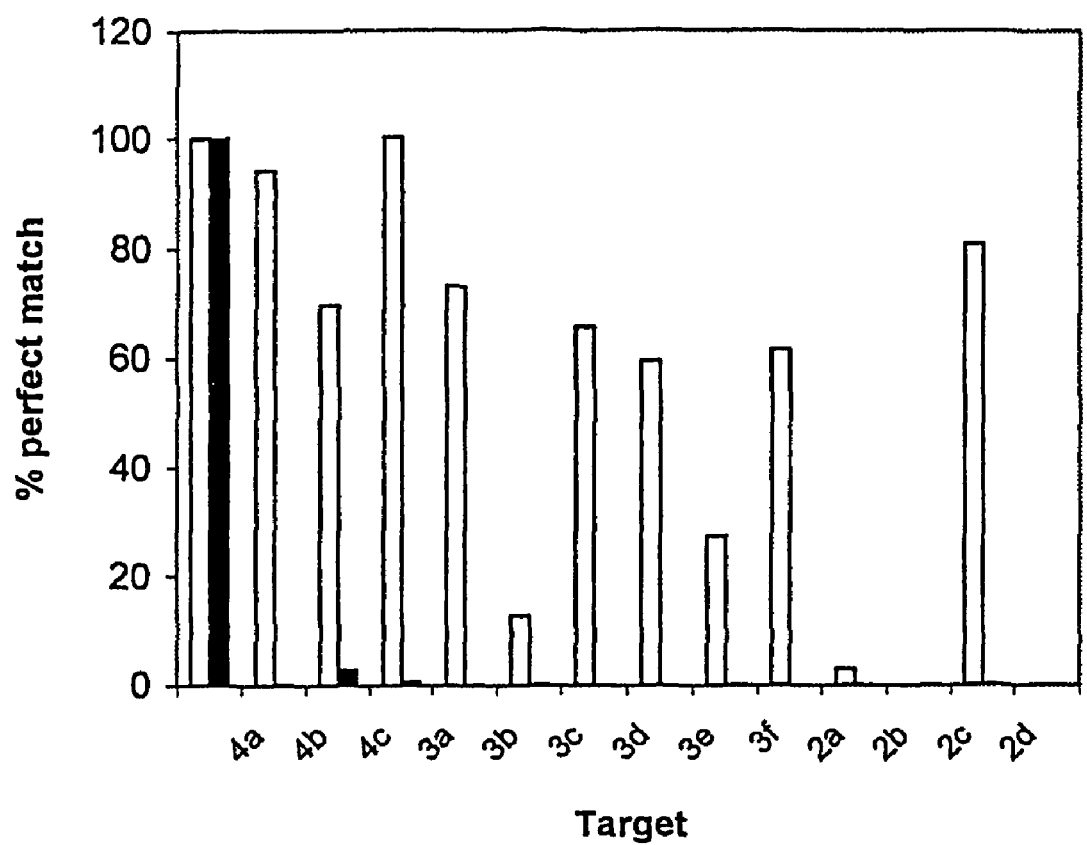
FIG. 10 is a bar graph showing relative hybridizations of different nucleic acid molecules with the capture probes having SEQ ID NO:34 (dark bars) and SEQ ID NO:35 (light bars) as described in Example 5. The percent hybridization of a nucleic acid sequence having a mismatch with each probe is plotted for each nucleic acid sequence, identified by the identifier given in FIG. 6 and Table 2, the first pair of bars being for the matching probe:target combinations.

Here, probes were biotinylated on their 5'-ends (indicated with an x in Table 2) to permit attachment to avidin-coated microtitre walls. The protocol outlined in Example 4 was thus followed with probes having SEQ ID NOs:34 and 35 and targets having SEQ ID NOs:20 to 33. The results are shown in FIG. 10.

As can be seen, the probe having a single hairpin in its target-binding region (SEQ ID NO:34) was able to discriminate between all thirteen mismatched targets when the arbitrary 10% perfect match intensity is used as a cutoff point. The probe lacking any hairpin structure (SEQ ID NO:35) was able to discriminate 3 (SEQ ID NOs:30, 31 and 33) of the 13 mismatched targets from the perfectly matched target (SEQ ID NO:20).

EXAMPLE 6

Probes of this invention will find application in the area of primed synthesis of nucleic acid molecules involving multiplexed (two or more) reactions. For example, probes of this invention can be used as primers in the polymerase chain reaction (PCR), genetic bit analysis (GBA), and the like.

In a multiplex PCR reaction, several primer pairs are present and the likelihood of generating undesired amplification products increases as the number of non-specific hybridization reactions between primer pairs and target increases. The use of appropriate probes of the invention as primers will reduce this problem by increasing the specificity of the priming steps of the PCR reaction. These primers will also permit primer annealing to occur at lower temperatures resulting in more efficient amplification (ie. greater sensitivity).

Figure 11:
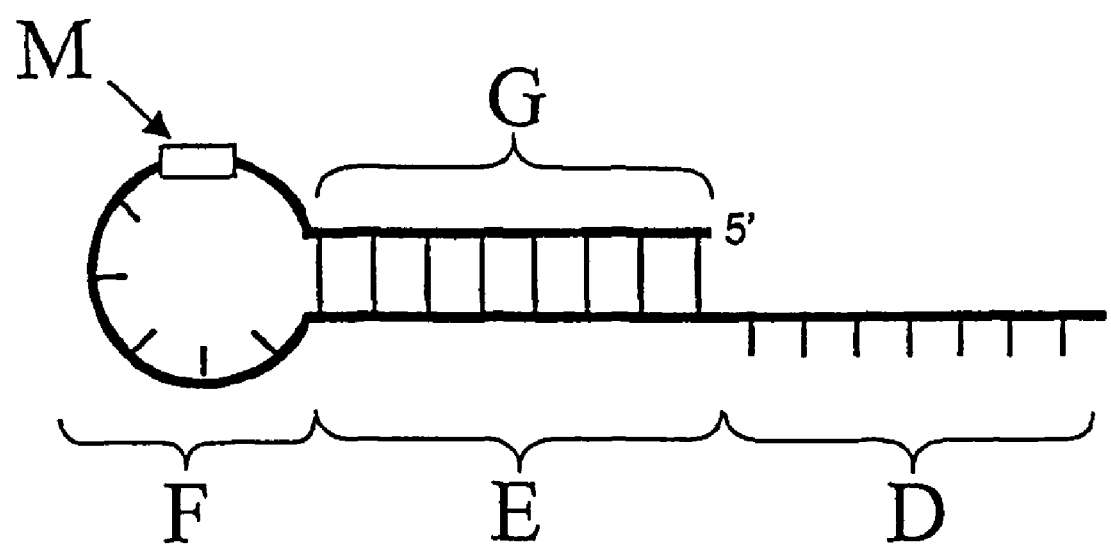
FIG. 11 is a schematic diagram showing a linear loop probe for use as a primer, as described in Example 6.
Figure 12A:
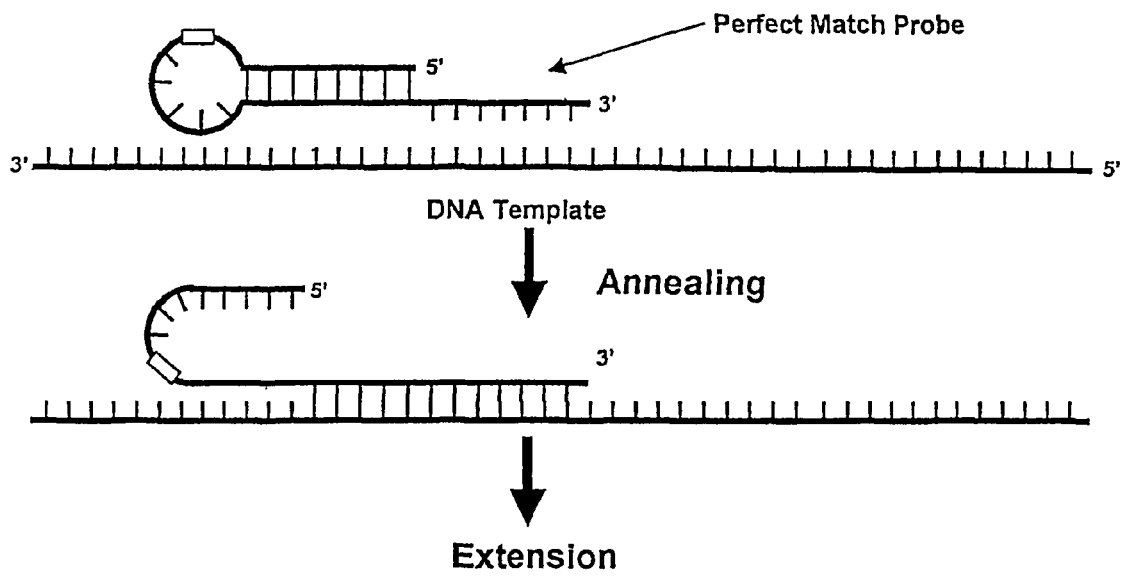
FIGS. 12A and 12B is a schematic illustrating the use of a nucleic acid capture moiety of the invention in priming synthesis in the presence of complex mixture of nucleic acid sequences.
Figure 12B:
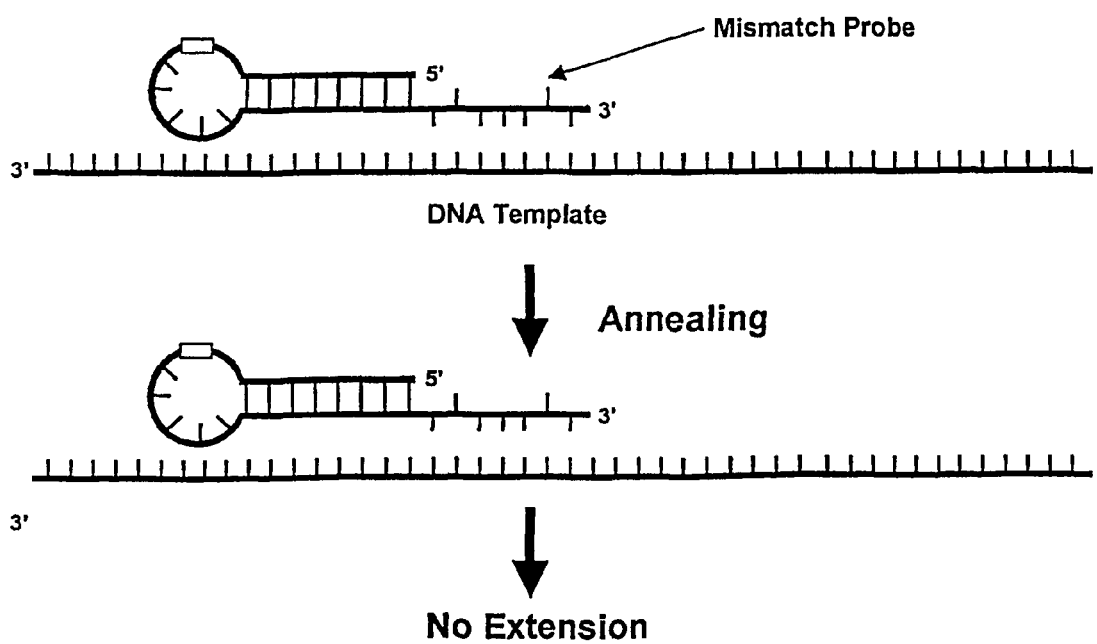

In one embodiment, primers having the general structure of the probe illustrated in FIG. 11 are used. Each primer is designed with the "target" end at the 3'-end of the probe, this orientation being dictated by the direction of strand synthesis. The 5'-end would include sequences E-F-G able to form a hairpin structure by hybridization between regions E and G, as illustrated. The probe also includes at least one sequence, preferably between four and six bases in length, designed to be single-stranded within in the probe and to act as a nucleation site for hybridization with the target. Region F (or a part thereof contiguous with region E) or region D can act as a nucleation site for the priming step, or both of these portions can be designed to act as nucleation sites. The looped structure can also include a modified nucleotide, indicated by 'M' in FIG. 11. This modified nucleotide can be selected so as to block extension of the 3'-end of the strand to be amplified by a polymerase such as Taq DNA polymerase during the PCR reaction. Additionally, or alternatively, the modified nucleotide can be selected to permit coupling of the primer to another entity, e.g., a biotin molecule or a solid support. Preferably, the $T_m$ of the primer-target duplex is higher than the $T_m$ of the hairpin of the primer loop structure for amplification to readily occur i.e., to permit opening of the hairpin upon nucleation and to discourage the hairpin from reforming once intermolecular hybridization has begun. It would also be advantageous for the $T_m$ of the hairpin to be higher than that of a potential intermolecular mismatched hybrid that might form, so as to discourage priming of such a mismatched target.

EXAMPLE 7

Probes of this invention will find application as members of a universal family of probes. A particular application includes the use of a family of $HP^2$ probes or a family of linear looped probes for discriminating between several closely related sequences present in multiplexed systems. Such a family could be included as part of a microarray or as part of a bead-based universal array. An example of one such system involves the Luminex[100] LabMAP technology which uses 100 spectrally distinct bead populations to simultaneously measure up to 100 different analytes in a single reaction. Each of the 100 different carboxylated bead populations could be coupled to a unique amino-modified probe of the present invention. In this way, a family of probes of the present invention comprises a family of "tags", as they are often referred to in the art. An example for covalently linking such a tag to a solid carboxylated bead support involves the use of 1-ethyl-3-(3-dimethylaminopropyl)-carbodiimide (EDC) as a cross-linking reagent in a buffer consisting of 0.1 M MES (2-(N-morpholino) ethane sulfonic acid) pH 4.5 or similar linking chemistry.

Target nucleic acid sequences such as genomic DNA, cDNA, mRNA and the like are purified by methods known in the art and can be further prepared by one of a number of front end chemistry approaches such as, but not limited to, PCR, Genetic Bit Analysis, Ligase Chain Reaction and the Invader Assay. Using these methods, the anti-tag sequence is either incorporated into a target related product or associated with the target through formation of a hybrid. For example, an assay may involve the generation of a labeled PCR product that is then hybridized to a complementary probe that is synthesized with the anti-tag sequence at one end of the probe. $HP^2$ or linear loop tag-coupled beads could then be hybridized to the anti-tag sequences that have been hybridized with specific targets. In addition, targets would be modified in such a way as to allow for capture of a fluorescent reporter. For example, targets could be biotinylated allowing for capture of a streptavidin-phycoerythrin conjugate. The fluorescent phycoerythrin molecule serves as the reporter detected by the Luminex[100] LabMAP system which quantifies the biomolecular interaction which has occurred at the bead surfaces.

Results actually obtained with probes having different structural characteristics are described in examples of this application. See FIGS. 1 to 10. While the examples described herein establish the feasibility of the approach of the present invention and the best approach known to the inventors at this time has been described, it is also very possible that even better results with other probes that fall within the scope of this invention can be obtained. For example, it has been demonstrated that region G (FIGS. 1A to 1D) of a probe can be six bases in length (Examples 1, 2 and 3) or it can be ten bases in length (Examples 4 and 5). It must also be borne in mind that there is a variety of factors to consider in developing a commercial product. For example, a shorter probe would usually be less expensive to produce than a longer probe. On the other hand, greater selectivity between probes of a large family of probes to be used together in a single application can be obtained using larger target-binding sites. There are many possible considerations to be had in the creation of a product for sale in the marketplace. The final approach taken to obtaining a product considered optimal for any particular application may well entail a probe that is quite different in detail than the specific probes used in the examples described herein while still retaining the inventive aspects created by the inventors.

A person skilled in the art will also understand that individual elements of the invention can be combined in a variety ways and are in the possession of the inventors, even if a particular inventive combination is mentioned herein only in combination with other elements that do not contribute to the inventiveness.

All documents referred to in this specification are incorporated herein by reference as though their entire contents were reproduced herein. Mention of a reference in this specification, however, is not a representation or an admission that such reference is prior art with respect to any invention described herein, regardless of the context in which the reference is mentioned.

Preferred embodiments and other aspects of the invention having been described, the scope of protection sought for the invention is defined by the following claims.

The invention claimed is:

1. A method of detecting a target nucleic acid sequence in a sample, the method comprising:
   (a) combining the sample under a defined set of conditions with a unimolecular probe comprising,
      (i) a first nucleic acid sequence complementary to the target nucleic acid sequence and comprising a first portion and a second portion,
      (ii) a second nucleic acid sequence complementary to the first portion of the first nucleic acid sequence and capable of hybridizing therewith to form a first intramolecular duplex comprising a first hairpin structure under the defined set of conditions, the first intramolecular duplex including a portion of the first nucleic acid sequence, wherein the portion of the first nucleic acid sequence of the first intramolecular duplex is capable of hybridizing to the target nucleic acid sequence, and
      (iii) third and fourth nucleic acid sequences being complementary to each other and linked to each other so as to hybridize to form a second intramolecular duplex comprising a second hairpin structure under said set of conditions, wherein the second portion of the first nucleic acid sequence comprises a single stranded region covalently attached to the third nucleic acid sequence and is located between the first and second intramolecular duplexes;
   (b) permitting the target nucleic acid sequence, if present in the sample, to hybridize with the first nucleic acid sequence under the defined set of conditions thereby disrupting the first intramolecular duplex and forming an intermolecular duplex comprising the target nucleic acid sequence and the first nucleic acid sequence; and
   (c) detecting the presence of the intermolecular duplex, wherein the presence of the intermolecular duplex is indicative of the presence of the target nucleic acid sequence in the sample.

2. The method of claim 1, wherein, during step (b), the single stranded region of the first nucleic acid sequence acts as a nucleation site of intermolecular duplex formation between the target nucleic acid sequence and the first nucleic acid sequence.

3. The method of claim 1, wherein the target nucleic acid sequence is a terminal sequence of a molecule, such that upon formation of the intermolecular duplex, the intermolecular duplex and the second intramolecular duplex form a nicked duplex.

4. The method of claim 1, wherein the third and fourth nucleic acid sequences are connected to each other by a single stranded nucleic acid sequence up to twenty bases in length, or up to eighteen bases in length, or up to sixteen bases in length, or up to fourteen bases in length, or up to twelve bases in length, or up to ten bases in length, or up to eight bases in length, or up to six bases in length, or at least two bases in length.

5. The method of claim 1, wherein the first intramolecular duplex is no longer than the second intramolecular duplex in length and the second intramolecular duplex has a GC content greater than that of the first intramolecular duplex.

6. The method of claim 1, wherein the first intramolecular duplex has a lower $T_m$ than the second intramolecular duplex under said defined set of conditions.

7. The method of claim 1, wherein the second intramolecular duplex is between three and thirty base pairs in length, or between three and twenty-five base pairs in length, or between six and twenty base pairs in length, or between ten and eighteen base pairs in length, or between fourteen and seventeen base pairs in length; or wherein the second intramolecular duplex is sixteen base pairs in length.

8. The method of claim 1, wherein the first nucleic acid sequence of the unimolecular probe is up to forty nucleic acid bases in length, or is up to thirty nucleic acid bases in length, or is up to twenty-six nucleic acid bases in length, or between six and forty nucleic acid bases in length, or between eight and thirty-five nucleic acid bases in length, or between ten and thirty nucleic acid bases in length, or between fifteen and thirty nucleic acid bases in length or between eighteen and twenty-eight nucleic acid bases in length, or between twenty and twenty-six nucleic acid bases in length; or wherein the first nucleic acid sequence is twenty-four nucleic acid bases in length.

9. The method of claim 1, wherein the second nucleic acid sequence of the unimolecular probe is at least four nucleic acid bases in length, or up to fourteen nucleic acid bases in length, or wherein the second nucleic acid sequence is between five and twelve nucleic acid bases in length, or between six and twelve nucleic acid bases in length, or between seven and twelve nucleic acid bases in length, or between eight and twelve nucleic acid bases in length, or between nine and twelve nucleic acid bases in length, or is ten nucleic acid bases in length.

10. A method of detecting a plurality of different target nucleic acid sequences in a sample, the method comprising:
(a) combining the sample under a defined set of conditions with a plurality of microparticles comprising a plurality of different probes, wherein each of the microparticles comprises one of the different probes and each of the different probes comprises,
  (i) a first tag sequence complementary to a specific target nucleic acid sequence of the plurality of different target nucleic acid sequences, and
  (ii) a nucleic acid second sequence complementary to a portion of the first tag sequence and capable of hybridization therewith to form a first intramolecular duplex under the defined set of conditions, the first intramolecular duplex including a portion of the first tag sequence, wherein the portion of the first tag sequence of the first intramolecular duplex is capable of hybridizing to the specific target nucleic acid sequence;
(b) permitting each of the plurality of different target nucleic acid sequences, if present in the sample, to hybridize with its complementary first tag sequence under the defined set of conditions, so as to disrupt the intramolecular duplex of each of the different probes and form different intermolecular duplexes, wherein each of the intermolecular duplexes comprises the specific target nucleic acid sequence and the first target sequence; and
(c) detecting the presence of the different intermolecular duplexes, wherein the presence of the different intermolecular duplexes is indicative of the presence of the different target nucleic acid sequences in the sample.

11. The method of claim 10, wherein the plurality of microparticles comprises at least ten different populations of microparticles.

12. The method of claim 11, wherein each of the different populations of said microparticles comprises a unique probe attached thereto for detection of a specific target nucleic acid sequence of the plurality of different target nucleic acid sequences, wherein the specific target nucleic acid sequence is different for each of the different populations of microparticles, and wherein the first tag sequence of the unique probe attached to each member of a population of said microparticles is identical.

13. The method of claim 11, wherein the first tag sequence in one population of said microparticles varies from the first tag sequence in every other population of said microparticles by least three bases.

14. The method of claim 10, wherein the first tag sequence is at least 10 nucleotides in length.

15. The method of claim 10, wherein the first tag sequence is from about 10 nucleotides in length to about 60 nucleotides in length.

16. The method of claim 10, wherein the entire duplex portion of the first tag sequence is complementary to the specific target nucleic acid sequence.

17. The method of claim 10, wherein the duplex portion of the first tag sequence complementary to the target nucleic acid sequence is between four and ten bases in length or between three and nine bases in length.

18. A method of detecting a target nucleic acid sequence in a sample, the method comprising:
(a) combining the sample under a defined set of conditions with a unimolecular probe comprising,
  (i) a first nucleic acid sequence complementary to the target nucleic acid sequence, and
  (ii) a second nucleic acid sequence complementary to a first portion of the first nucleic acid sequence and capable of hybridization therewith to form a first intramolecular duplex comprising a first hairpin structure under the defined set of conditions, the first intramolecular duplex including a portion of the first nucleic acid sequence, wherein the portion of the first nucleic acid sequence of the first intramolecular duplex is capable of hybridizing to the target nucleic acid sequence, and
  (iii) third and fourth nucleic acid sequences being complementary to each other and linked to each other so as to hybridize to form a second intramolecular duplex comprising a second hairpin structure under said set of conditions, wherein the third nucleic acid sequence is covalently attached to one end of the first nucleic acid;
(b) permitting the target nucleic acid sequence, if present in the sample, to hybridize with the first nucleic acid sequence under the defined set of conditions, thereby disrupting the first intramolecular duplex to form an intermolecular duplex comprising the target nucleic acid sequence and the first nucleic acid sequence; and
(c) detecting the presence of the intermolecular duplex, wherein the presence of the intermolecular duplex is indicative of the presence of the target nucleic acid in the sample.

19. The method of claim 18, wherein the first nucleic acid sequence of the unimolecular probe comprises a single-stranded region located between the first and second intramolecular duplexes.

20. The method of claim 19, wherein, during step (b), the single-stranded region of the unimolecular probe acts as a nucleation site of intermolecular duplex formation between the target nucleic acid sequence and the first nucleic acid sequence.

21. The method of claim 20, wherein the target nucleic acid sequence is a terminal sequence of a molecule, such that upon formation of the intermolecular duplex, the intermolecular duplex and the second intramolecular duplex form a nicked duplex.

22. The method of claim 18, wherein the third and fourth nucleic acid sequences of the unimolecular probe are connected to each other by a single stranded nucleic acid sequence up to twenty bases in length, or up to eighteen bases in length, or up to sixteen bases in length, or up to fourteen bases in length, or up to twelve bases in length, or up to ten bases in length, or up to eight bases in length, or up to six bases in length, or at least two bases in length.

23. The method of claim 18, wherein the first intramolecular duplex of the unimolecular probe is no longer than the second intramolecular duplex in length and the second intramolecular duplex has a GC content greater than that of the first intramolecular duplex.

24. The method of claim 18, wherein the first intramolecular duplex of the unimolecular probe has a lower $T_m$ than the second intramolecular duplex under said set of conditions.

25. The method of claim 18, wherein the second intramolecular duplex of the unimolecular probe is between three and thirty base pairs in length, or between three and twenty-five base pairs in length, or between six and twenty base pairs in length, or between ten and eighteen base pairs in length, or between fourteen and seventeen base pairs in length; or wherein the second intramolecular duplex is sixteen base pairs in length.

26. The method of claim 18, wherein the first nucleic acid sequence of the unimolecular probe is up to forty nucleic acid bases in length, or is up to thirty nucleic acid bases in length, or is up to twenty-six nucleic acid bases in length, or between six and forty nucleic acid bases in length, or between eight and thirty-five nucleic acid bases in length, or between ten and thirty nucleic acid bases in length, or between fifteen and thirty nucleic acid bases in length or between eighteen and twenty-eight nucleic acid bases in length, or between twenty and twenty-six nucleic acid bases in length; or wherein the first nucleic acid sequence is twenty-four nucleic acid bases in length.

27. The method of claim 18, wherein the second nucleic acid sequence of the unimolecular probe is at least four nucleic acid bases in length, or up to fourteen nucleic acid bases in length, or wherein the second nucleic acid sequence is between five and twelve nucleic acid bases in length, or between six and twelve nucleic acid bases in length, or between seven and twelve nucleic acid bases in length, or between eight and twelve nucleic acid bases in length, or between nine and twelve nucleic acid bases in length, or is ten nucleic acid bases in length.

* * * * *

SEQUENCE LISTING

<160> NUMBER OF SEQ ID NOS: 35

<210> SEQ ID NO 1
<211> LENGTH: 59
<212> TYPE: DNA
<213> ORGANISM: Artificial Sequence
<220> FEATURE:
<223> OTHER INFORMATION: Artificially Synthesized Nucleic Acid Probe

<400> SEQUENCE: 1
gaagcacaca caacactttt tgtgttgtgt gtgcttcaca gatcccctag acaagggga    59

<210> SEQ ID NO 2
<211> LENGTH: 59
<212> TYPE: DNA
<213> ORGANISM: Artificial Sequence
<220> FEATURE:
<223> OTHER INFORMATION: Artificially Synthesized Nucleic Acid Probe

<400> SEQUENCE: 2
gaagcacaca caacactttt tgtgttgtgt gtgcttcaca gatcccctag acaaaaaaa    59

<210> SEQ ID NO 3
<211> LENGTH: 16
<212> TYPE: DNA
<213> ORGANISM: Artificial Sequence
<220> FEATURE:
<223> OTHER INFORMATION: Target nucleic acid sequence

<400> SEQUENCE: 3
tgtctagggg atctgt    16

<210> SEQ ID NO 4
<211> LENGTH: 16
<212> TYPE: DNA
<213> ORGANISM: Artificial Sequence
<220> FEATURE:
<223> OTHER INFORMATION: Target nucleic acid sequence

<400> SEQUENCE: 4
tgtctagggg atgtgt    16

<210> SEQ ID NO 5
<211> LENGTH: 16
<212> TYPE: DNA
<213> ORGANISM: Artificial Sequence
<220> FEATURE:
<223> OTHER INFORMATION: Target nucleic acid sequence

<400> SEQUENCE: 5
tgtctagggg aactgt    16

<210> SEQ ID NO 6
<211> LENGTH: 16
<212> TYPE: DNA
<213> ORGANISM: Artificial Sequence
<220> FEATURE:
<223> OTHER INFORMATION: Target nucleic acid sequence

<400> SEQUENCE: 6
tgtctagggg gtctgt    16

<210> SEQ ID NO 7
<211> LENGTH: 16
<212> TYPE: DNA

```
<213> ORGANISM: Artificial Sequence
<220> FEATURE:
<223> OTHER INFORMATION: Target nucleic acid sequence

<400> SEQUENCE: 7
tgtctaggga atctgt                                                        16

<210> SEQ ID NO 8
<211> LENGTH: 16
<212> TYPE: DNA
<213> ORGANISM: Artificial Sequence
<220> FEATURE:
<223> OTHER INFORMATION: Target nucleic acid sequence

<400> SEQUENCE: 8
tgtctaggag atctgt                                                        16

<210> SEQ ID NO 9
<211> LENGTH: 16
<212> TYPE: DNA
<213> ORGANISM: Artificial Sequence
<220> FEATURE:
<223> OTHER INFORMATION: Target nucleic acid sequence

<400> SEQUENCE: 9
tgtctagagg atctgt                                                        16

<210> SEQ ID NO 10
<211> LENGTH: 16
<212> TYPE: DNA
<213> ORGANISM: Artificial Sequence
<220> FEATURE:
<223> OTHER INFORMATION: Target nucleic acid sequence

<400> SEQUENCE: 10
tgtctaaggg atctgt                                                        16

<210> SEQ ID NO 11
<211> LENGTH: 16
<212> TYPE: DNA
<213> ORGANISM: Artificial Sequence
<220> FEATURE:
<223> OTHER INFORMATION: Target nucleic acid sequence

<400> SEQUENCE: 11
tgtctggggg atctgt                                                        16

<210> SEQ ID NO 12
<211> LENGTH: 16
<212> TYPE: DNA
<213> ORGANISM: Artificial Sequence
<220> FEATURE:
<223> OTHER INFORMATION: Target nucleic acid sequence

<400> SEQUENCE: 12
tgtcaagggg atctgt                                                        16

<210> SEQ ID NO 13
<211> LENGTH: 16
<212> TYPE: DNA
<213> ORGANISM: Artificial Sequence
<220> FEATURE:
<223> OTHER INFORMATION: Target nucleic acid sequence

<400> SEQUENCE: 13
tgtgtagggg atctgt                                                        16
```

-continued

<210> SEQ ID NO 14
<211> LENGTH: 40
<212> TYPE: DNA
<213> ORGANISM: Artificial Sequence
<220> FEATURE:
<223> OTHER INFORMATION: Artificially Synthesized Nucleic Acid Probe

<400> SEQUENCE: 14
ttgtgttgtg tgtgcttcac agatccccta gacaagggga                40

<210> SEQ ID NO 15
<211> LENGTH: 59
<212> TYPE: DNA
<213> ORGANISM: Artificial Sequence
<220> FEATURE:
<223> OTHER INFORMATION: Artificially Synthesized Nucleic Acid Probe

<400> SEQUENCE: 15
gaagcacaca caacactttt tgtgttgtgt gtgcttcact gatcccctag tcaagggga    59

<210> SEQ ID NO 16
<211> LENGTH: 59
<212> TYPE: DNA
<213> ORGANISM: Artificial Sequence
<220> FEATURE:
<223> OTHER INFORMATION: Artificially Synthesized Nucleic Acid Probe

<400> SEQUENCE: 16
gaagcacaca caacactttt tgtgttgtgt gtgcttcact gatcccctag tcaaaaaaa    59

<210> SEQ ID NO 17
<211> LENGTH: 16
<212> TYPE: DNA
<213> ORGANISM: Artificial Sequence
<220> FEATURE:
<223> OTHER INFORMATION: Target nucleic acid sequence

<400> SEQUENCE: 17
tgactagggg atcagt                16

<210> SEQ ID NO 18
<211> LENGTH: 63
<212> TYPE: DNA
<213> ORGANISM: Artificial Sequence
<220> FEATURE:
<223> OTHER INFORMATION: Artificially Synthesized Nucleic Acid Probe

<400> SEQUENCE: 18
ctataccaca ccttttttggt gtggtatagt gattgtattg agatttgatt gtaaaatctc    60
aat                63

<210> SEQ ID NO 19
<211> LENGTH: 53
<212> TYPE: DNA
<213> ORGANISM: Artificial Sequence
<220> FEATURE:
<223> OTHER INFORMATION: Artificially Synthesized Nucleic Acid Probe

<400> SEQUENCE: 19
ctataccaca ccttttttggt gtggtatagt gattgtattg agatttgatt gta            53

<210> SEQ ID NO 20
<211> LENGTH: 24
<212> TYPE: DNA
<213> ORGANISM: Artificial Sequence
<220> FEATURE:

```
<223> OTHER INFORMATION: Target nucleic acid sequence

<400> SEQUENCE: 20
tacaatcaaa tctcaataca atca                                              24

<210> SEQ ID NO 21
<211> LENGTH: 24
<212> TYPE: DNA
<213> ORGANISM: Artificial Sequence
<220> FEATURE:
<223> OTHER INFORMATION: Target nucleic acid sequence

<400> SEQUENCE: 21
ctttatacaa tctcaataca atca                                              24

<210> SEQ ID NO 22
<211> LENGTH: 24
<212> TYPE: DNA
<213> ORGANISM: Artificial Sequence
<220> FEATURE:
<223> OTHER INFORMATION: Target nucleic acid sequence

<400> SEQUENCE: 22
ctttatcaaa tctcaataca atac                                              24

<210> SEQ ID NO 23
<211> LENGTH: 24
<212> TYPE: DNA
<213> ORGANISM: Artificial Sequence
<220> FEATURE:
<223> OTHER INFORMATION: Target nucleic acid sequence

<400> SEQUENCE: 23
tacaatcaaa tctcaacttt atac                                              24

<210> SEQ ID NO 24
<211> LENGTH: 24
<212> TYPE: DNA
<213> ORGANISM: Artificial Sequence
<220> FEATURE:
<223> OTHER INFORMATION: Target nucleic acid sequence

<400> SEQUENCE: 24
ctttatcaat actcaataca atca                                              24

<210> SEQ ID NO 25
<211> LENGTH: 24
<212> TYPE: DNA
<213> ORGANISM: Artificial Sequence
<220> FEATURE:
<223> OTHER INFORMATION: Target nucleic acid sequence

<400> SEQUENCE: 25
tacactttat actcaataca atca                                              24

<210> SEQ ID NO 26
<211> LENGTH: 24
<212> TYPE: DNA
<213> ORGANISM: Artificial Sequence
<220> FEATURE:
<223> OTHER INFORMATION: Target nucleic acid sequence

<400> SEQUENCE: 26
tacactttaa tctcaataca atac                                              24

<210> SEQ ID NO 27
```

```
<211> LENGTH: 24
<212> TYPE: DNA
<213> ORGANISM: Artificial Sequence
<220> FEATURE:
<223> OTHER INFORMATION: Target nucleic acid sequence

<400> SEQUENCE: 27
ctttatcaaa tctcaaatac atca                                              24

<210> SEQ ID NO 28
<211> LENGTH: 24
<212> TYPE: DNA
<213> ORGANISM: Artificial Sequence
<220> FEATURE:
<223> OTHER INFORMATION: Target nucleic acid sequence

<400> SEQUENCE: 28
tacaatcaaa tcatactaca cttt                                              24

<210> SEQ ID NO 29
<211> LENGTH: 24
<212> TYPE: DNA
<213> ORGANISM: Artificial Sequence
<220> FEATURE:
<223> OTHER INFORMATION: Target nucleic acid sequence

<400> SEQUENCE: 29
tacaatcaaa tcctttatac atca                                              24

<210> SEQ ID NO 30
<211> LENGTH: 24
<212> TYPE: DNA
<213> ORGANISM: Artificial Sequence
<220> FEATURE:
<223> OTHER INFORMATION: Target nucleic acid sequence

<400> SEQUENCE: 30
ctttatcaaa tcatactaca atca                                              24

<210> SEQ ID NO 31
<211> LENGTH: 24
<212> TYPE: DNA
<213> ORGANISM: Artificial Sequence
<220> FEATURE:
<223> OTHER INFORMATION: Target nucleic acid sequence

<400> SEQUENCE: 31
tacaatcact ttatactaca atca                                              24

<210> SEQ ID NO 32
<211> LENGTH: 24
<212> TYPE: DNA
<213> ORGANISM: Artificial Sequence
<220> FEATURE:
<223> OTHER INFORMATION: Target nucleic acid sequence

<400> SEQUENCE: 32
tacaatcaat actcaataca cttt                                              24

<210> SEQ ID NO 33
<211> LENGTH: 24
<212> TYPE: DNA
<213> ORGANISM: Artificial Sequence
<220> FEATURE:
<223> OTHER INFORMATION: Target nucleic acid sequence

<400> SEQUENCE: 33
```

```
tacactttaa tctcaaatac atca                                              24
```

<210> SEQ ID NO 34
<211> LENGTH: 34
<212> TYPE: DNA
<213> ORGANISM: Artificial Sequence
<220> FEATURE:
<223> OTHER INFORMATION: Artificially Synthesized Nucleic Acid Probe

<400> SEQUENCE: 34

```
tgattgtatt gagatttgat tgtaaaatct caat                                   34
```

<210> SEQ ID NO 35
<211> LENGTH: 24
<212> TYPE: DNA
<213> ORGANISM: Artificial Sequence
<220> FEATURE:
<223> OTHER INFORMATION: Artificially Synthesized Nucleic Acid Probe

<400> SEQUENCE: 35

```
tgattgtatt gagatttgat tgta                                              24
```